United States Patent
Carson

(10) Patent No.: US 9,687,386 B2
(45) Date of Patent: Jun. 27, 2017

(54) COOLING MEDICAL PAD

(75) Inventor: Gary A. Carson, Golden, CO (US)

(73) Assignee: Medivance Incorporated, Louisville, CO (US)

( * ) Notice: Subject to any disclaimer, the term of this patent is extended or adjusted under 35 U.S.C. 154(b) by 1434 days.

(21) Appl. No.: 13/230,663

(22) Filed: Sep. 12, 2011

(65) Prior Publication Data

US 2012/0065715 A1 Mar. 15, 2012

Related U.S. Application Data

(60) Provisional application No. 61/389,056, filed on Oct. 1, 2010, provisional application No. 61/381,840, filed on Sep. 10, 2010.

(51) Int. Cl.
*A61F 7/00* (2006.01)
*A61F 7/08* (2006.01)
*A61F 7/10* (2006.01)
*A61F 7/02* (2006.01)

(52) U.S. Cl.
CPC ........ *A61F 7/10* (2013.01); *A61F 2007/0056* (2013.01); *A61F 2007/0219* (2013.01); *A61F 2007/0226* (2013.01); *A61F 2007/0247* (2013.01)

(58) Field of Classification Search
CPC ................ A61F 7/10; A61F 2007/0056; A61F 2007/0244; A61F 2007/0246; A61F 2007/0247
See application file for complete search history.

(56) References Cited

U.S. PATENT DOCUMENTS

| | | |
|---|---|---|
| 2,250,325 A | 7/1941 | Barnes |
| 2,595,328 A | 5/1952 | Bowen |
| 2,602,302 A | 7/1952 | Poux |
| 2,726,658 A | 12/1955 | Chessey |
| 3,075,529 A | 1/1963 | Young |
| 3,091,242 A | 5/1963 | Johnson, Jr. et al. |
| 3,212,286 A | 10/1965 | Curtis |
| 3,506,013 A | 4/1970 | Zdenek |
| 3,734,293 A | 5/1973 | Biskis |
| 3,830,676 A | 8/1974 | Elkins |
| 3,867,939 A | 2/1975 | Moore et al. |
| 3,900,035 A | 8/1975 | Welch et al. |
| 3,927,671 A | 12/1975 | Chittenden et al. |
| 3,995,621 A | 12/1976 | Fletcher et al. |

(Continued)

FOREIGN PATENT DOCUMENTS

| | | |
|---|---|---|
| TW | 2204150 A1 | 7/2010 |
| WO | PCT/IL99/00059 A1 | 9/1999 |
| WO | PCT/US03/010311 A2 | 10/2003 |

*Primary Examiner* — Kaitlyn Smith
(74) *Attorney, Agent, or Firm* — Marsh Fischmann & Breyfogle LLP

(57) ABSTRACT

A medical pad has multiple layers. A first layer is for containing a first thermal-exchange fluid circulatable therethrough, with the medical pad being operable for thermal exchange between the first thermal-exchange fluid and a patient through a first side of the first layer. A second layer of the medical pad is interconnected to a second side of the first layer, opposite to the first side of the first layer. The second layer encloses a second thermal-exchange fluid that may have a freezing point of 0° C. or less. The medical pad is operable for thermal exchange between the second thermal-exchange fluid and the patient.

29 Claims, 15 Drawing Sheets

(56) References Cited

U.S. PATENT DOCUMENTS

| | | |
|---|---|---|
| 4,092,982 A | 6/1978 | Salem |
| 4,108,146 A | 8/1978 | Golden |
| 4,114,620 A | 9/1978 | Moore et al. |
| 4,118,946 A | 10/1978 | Tubin |
| 4,149,541 A | 4/1979 | Gammons et al. |
| 4,154,245 A | 5/1979 | Daily |
| 4,161,210 A | 7/1979 | Reid et al. |
| 4,195,631 A | 4/1980 | Baucom |
| 4,311,022 A | 1/1982 | Hall |
| 4,444,727 A | 4/1984 | Yanagihara et al. |
| 4,508,123 A | 4/1985 | Wyatt et al. |
| 4,580,408 A | 4/1986 | Stuebner |
| 4,753,241 A | 6/1988 | Brannigan et al. |
| 4,834,705 A | 5/1989 | Vaillancourt |
| 4,846,176 A * | 7/1989 | Golden ............ 607/104 |
| 4,886,063 A | 12/1989 | Crews |
| 4,908,248 A | 3/1990 | Nakashima et al. |
| 4,919,134 A | 4/1990 | Streeter |
| 4,962,761 A * | 10/1990 | Golden ............ A61F 7/02 165/46 |
| 4,981,135 A | 1/1991 | Hardy |
| 4,989,607 A | 2/1991 | Keusch et al. |
| 5,000,252 A | 3/1991 | Faghri |
| 5,005,374 A | 4/1991 | Spitler |
| 5,050,596 A | 9/1991 | Walasek et al. |
| 5,062,414 A | 11/1991 | Grim |
| 5,072,875 A * | 12/1991 | Zacoi ............ 607/104 |
| 5,097,829 A | 3/1992 | Quisenberry |
| 5,111,668 A | 5/1992 | Parrish et al. |
| 5,113,666 A | 5/1992 | Parrish et al. |
| 5,133,348 A | 7/1992 | Mayn |
| 5,146,625 A | 9/1992 | Steele et al. |
| 5,190,032 A | 3/1993 | Zacoi |
| 5,265,669 A | 11/1993 | Schneider |
| 5,268,022 A | 12/1993 | Garrett et al. |
| 5,289,695 A | 3/1994 | Parrish et al. |
| 5,304,213 A | 4/1994 | Berke et al. |
| 5,304,216 A | 4/1994 | Wallace |
| 5,383,919 A | 1/1995 | Kelly et al. |
| 5,393,462 A * | 2/1995 | Avery ............ 516/102 |
| 5,405,366 A | 4/1995 | Fox et al. |
| 5,407,421 A * | 4/1995 | Goldsmith ............ A61F 5/012 128/882 |
| 5,409,500 A | 4/1995 | Dyrek |
| 5,411,541 A * | 5/1995 | Bell et al. ............ 607/104 |
| 5,423,751 A | 6/1995 | Harrison et al. |
| 5,456,701 A * | 10/1995 | Stout ............ 607/104 |
| 5,466,250 A | 11/1995 | Johnson, Jr. et al. |
| 5,470,353 A | 11/1995 | Jensen |
| 5,484,448 A | 1/1996 | Steele et al. |
| 5,486,207 A | 1/1996 | Mahawili |
| 5,514,169 A | 5/1996 | Dickerhoff et al. |
| 5,545,194 A | 8/1996 | Augustine |
| 5,605,144 A | 2/1997 | Simmons et al. |
| 5,609,620 A | 3/1997 | Daily |
| 5,624,477 A | 4/1997 | Armond |
| 5,634,940 A * | 6/1997 | Panyard ............ 607/104 |
| 5,640,728 A * | 6/1997 | Graebe ............ 5/606 |
| 5,658,325 A | 8/1997 | Augustine |
| 5,662,695 A | 9/1997 | Mason et al. |
| 5,683,439 A | 11/1997 | Jensen |
| 5,733,318 A | 3/1998 | Augustine |
| 5,755,755 A * | 5/1998 | Panyard ............ 607/104 |
| 5,806,335 A | 9/1998 | Herbert et al. |
| 5,837,002 A * | 11/1998 | Augustine et al. ............ 607/104 |
| 5,840,080 A | 11/1998 | Der Ovanesian |
| 5,843,145 A | 12/1998 | Brink |
| 5,887,437 A | 3/1999 | Maxim |
| 5,913,849 A | 6/1999 | Sundstrom et al. |
| 6,010,528 A * | 1/2000 | Augustine et al. ............ 607/104 |
| 6,019,783 A | 2/2000 | Philips et al. |
| 6,030,412 A * | 2/2000 | Klatz et al. ............ 607/104 |
| 6,047,106 A | 4/2000 | Salyer |
| 6,074,415 A | 6/2000 | Der Ovanesian |
| 6,083,256 A | 7/2000 | Der Ovanesian |
| 6,083,418 A | 7/2000 | Czarnecki et al. |
| 6,117,164 A | 9/2000 | Gildersleeve et al. |
| 6,185,744 B1 | 2/2001 | Poholski |
| 6,189,149 B1 | 2/2001 | Allen |
| 6,197,045 B1 | 3/2001 | Carson |
| 6,238,427 B1 | 5/2001 | Matta |
| 6,257,011 B1 | 7/2001 | Siman-Tov et al. |
| 6,349,560 B1 | 2/2002 | Maier-Laxhuber et al. |
| 6,364,937 B1 | 4/2002 | McMahon |
| 6,371,976 B1 * | 4/2002 | Vrzalik et al. ............ 607/104 |
| 6,375,674 B1 | 4/2002 | Carson |
| 6,389,839 B1 | 5/2002 | Sabin |
| 6,436,130 B1 | 8/2002 | Philips et al. |
| 6,454,792 B1 | 9/2002 | Noda et al. |
| 6,461,379 B1 * | 10/2002 | Carson et al. ............ 607/104 |
| 6,463,212 B1 | 10/2002 | Salyer |
| 6,503,297 B1 | 1/2003 | Lu et al. |
| 6,508,831 B1 | 1/2003 | Kushnir |
| 6,508,859 B1 | 1/2003 | Zia et al. |
| 6,511,502 B2 | 1/2003 | Fletcher |
| 6,559,096 B1 | 5/2003 | Smith et al. |
| 6,584,797 B1 | 7/2003 | Smith et al. |
| 6,591,630 B2 | 7/2003 | Smith et al. |
| 6,601,404 B1 | 8/2003 | Roderick |
| 6,620,187 B2 | 9/2003 | Carson et al. |
| 6,645,232 B2 | 11/2003 | Carson |
| 6,669,715 B2 | 12/2003 | Hoglund et al. |
| 6,682,525 B2 | 1/2004 | Lalonde et al. |
| 6,688,132 B2 | 2/2004 | Smith et al. |
| 6,692,518 B2 | 2/2004 | Carson |
| 6,701,724 B2 | 3/2004 | Smith et al. |
| 6,743,250 B2 | 6/2004 | Renfro |
| 6,755,801 B2 | 6/2004 | Utterberg et al. |
| 6,755,852 B2 | 6/2004 | Lachenbruch et al. |
| 6,800,087 B2 | 10/2004 | Papay et al. |
| 6,802,855 B2 | 10/2004 | Ellingboe et al. |
| 6,818,012 B2 | 11/2004 | Ellingboe |
| 6,858,068 B2 | 2/2005 | Smith et al. |
| 6,878,156 B1 | 4/2005 | Noda |
| 6,904,956 B2 | 6/2005 | Noel |
| 6,909,074 B1 | 6/2005 | Bradley |
| 6,931,875 B1 | 8/2005 | Allen et al. |
| 6,960,243 B1 | 11/2005 | Smith et al. |
| 6,968,711 B2 | 11/2005 | Smith et al. |
| 6,969,399 B2 | 11/2005 | Schock et al. |
| 7,008,445 B2 | 3/2006 | Lennox |
| 7,022,099 B2 | 4/2006 | Litzie et al. |
| 7,052,509 B2 | 5/2006 | Lennox et al. |
| 7,055,575 B2 | 6/2006 | Noel |
| 7,063,718 B2 | 6/2006 | Dobak, III |
| 7,077,858 B2 | 7/2006 | Fletcher et al. |
| 7,097,657 B2 | 8/2006 | Noda et al. |
| 7,172,586 B1 | 2/2007 | Dae et al. |
| 7,240,720 B2 | 7/2007 | Noel |
| 7,303,554 B2 | 12/2007 | Lalonde et al. |
| 7,303,579 B2 | 12/2007 | Schock et al. |
| 7,338,516 B2 | 3/2008 | Quincy, III et al. |
| 7,377,935 B2 | 5/2008 | Schock et al. |
| 7,507,250 B2 | 3/2009 | Lennox |
| RE40,815 E | 6/2009 | Kudaravalli et al. |
| 7,547,320 B2 | 6/2009 | Schook et al. |
| RE40,868 E | 8/2009 | Ryba et al. |
| 7,621,944 B2 | 11/2009 | Wilson et al. |
| 7,621,945 B2 | 11/2009 | Lennox et al. |
| 7,666,213 B2 | 2/2010 | Freedman, Jr. et al. |
| 7,678,716 B2 | 3/2010 | Yahiaoui et al. |
| 7,686,840 B2 | 3/2010 | Quincy, III et al. |
| 7,727,228 B2 | 6/2010 | Abboud et al. |
| 7,731,739 B2 | 6/2010 | Schock et al. |
| 7,744,640 B1 * | 6/2010 | Faries et al. ............ 607/109 |
| 7,763,061 B2 | 7/2010 | Schorr et al. |
| 7,771,461 B2 | 8/2010 | Schock et al. |
| 7,799,063 B2 | 9/2010 | Ingram et al. |
| 7,827,815 B2 | 11/2010 | Carson et al. |
| 7,896,910 B2 * | 3/2011 | Schirrmacher et al. ............ 607/104 |
| 8,047,010 B2 | 11/2011 | Carson et al. |
| 8,597,217 B2 * | 12/2013 | Lowe et al. ............ 602/13 |
| 2003/0109911 A1 * | 6/2003 | Lachenbruch et al. ............ 607/112 |
| 2003/0149461 A1 | 8/2003 | Johnson |

(56) References Cited

U.S. PATENT DOCUMENTS

| | | |
|---|---|---|
| 2003/0150232 A1 | 8/2003 | Brudnicki |
| 2004/0064170 A1* | 4/2004 | Radons et al. ............... 607/104 |
| 2004/0082886 A1* | 4/2004 | Timpson ..................... 601/15 |
| 2004/0243122 A1* | 12/2004 | Auth et al. ................... 606/41 |
| 2005/0060012 A1* | 3/2005 | Voorhees et al. ............ 607/96 |
| 2005/0096714 A1* | 5/2005 | Freedman et al. ........... 607/104 |
| 2005/0187502 A1* | 8/2005 | Krempel et al. ............. 602/5 |
| 2005/0244629 A1 | 11/2005 | Usui et al. |
| 2005/0288749 A1* | 12/2005 | Lachenbruch ............... 607/108 |
| 2006/0030916 A1 | 2/2006 | Lennox |
| 2006/0036304 A1 | 2/2006 | Cordani et al. |
| 2006/0074469 A1 | 4/2006 | Lennox et al. |
| 2006/0124141 A1 | 6/2006 | Dobak, III |
| 2006/0136023 A1 | 6/2006 | Dobak, III |
| 2006/0161232 A1 | 7/2006 | Kasza et al. |
| 2006/0247744 A1 | 11/2006 | Nest et al. |
| 2006/0276089 A1 | 12/2006 | Amarasinghe et al. |
| 2006/0287697 A1 | 12/2006 | Lennox |
| 2007/0043409 A1 | 2/2007 | Brian, III et al. |
| 2007/0049997 A1* | 3/2007 | Fields et al. ................. 607/96 |
| 2007/0054122 A1 | 3/2007 | Paisner et al. |
| 2007/0225782 A1 | 9/2007 | Taylor |
| 2007/0270925 A1 | 11/2007 | Levinson |
| 2008/0027523 A1 | 1/2008 | Behringer et al. |
| 2008/0249524 A1* | 10/2008 | Dunning ..................... 606/41 |
| 2008/0255644 A1* | 10/2008 | Carson ........................ 607/104 |
| 2008/0275534 A1 | 11/2008 | Noel |
| 2009/0088825 A1 | 4/2009 | Ota |
| 2009/0099629 A1 | 4/2009 | Carson et al. |
| 2009/0131835 A1 | 5/2009 | Voorhees et al. |
| 2009/0177184 A1* | 7/2009 | Christensen et al. ........ 604/506 |
| 2009/0287283 A1* | 11/2009 | Biser et al. ................. 607/109 |
| 2009/0326619 A1 | 12/2009 | Kagan |
| 2010/0016933 A1 | 1/2010 | Chen et al. |
| 2010/0168825 A1 | 7/2010 | Barbknecht et al. |
| 2010/0198122 A1 | 8/2010 | Freund |
| 2011/0029051 A1* | 2/2011 | Ross ........................... 607/108 |
| 2011/0306972 A1* | 12/2011 | Widenhouse et al. ....... 606/45 |
| 2011/0308781 A1 | 12/2011 | O'Riordan et al. |
| 2011/0313497 A1 | 12/2011 | McFarlane |
| 2012/0046720 A1 | 2/2012 | Ishizaki |
| 2012/0065715 A1 | 3/2012 | Carson |
| 2012/0191035 A1* | 7/2012 | Stephan ....................... 604/23 |
| 2012/0220960 A1 | 8/2012 | Ruland |
| 2013/0116760 A1* | 5/2013 | Carson et al. ............... 607/104 |
| 2014/0214138 A1* | 7/2014 | Voorhees et al. ............ 607/104 |
| 2014/0277301 A1* | 9/2014 | Varga et al. ................. 607/104 |

* cited by examiner

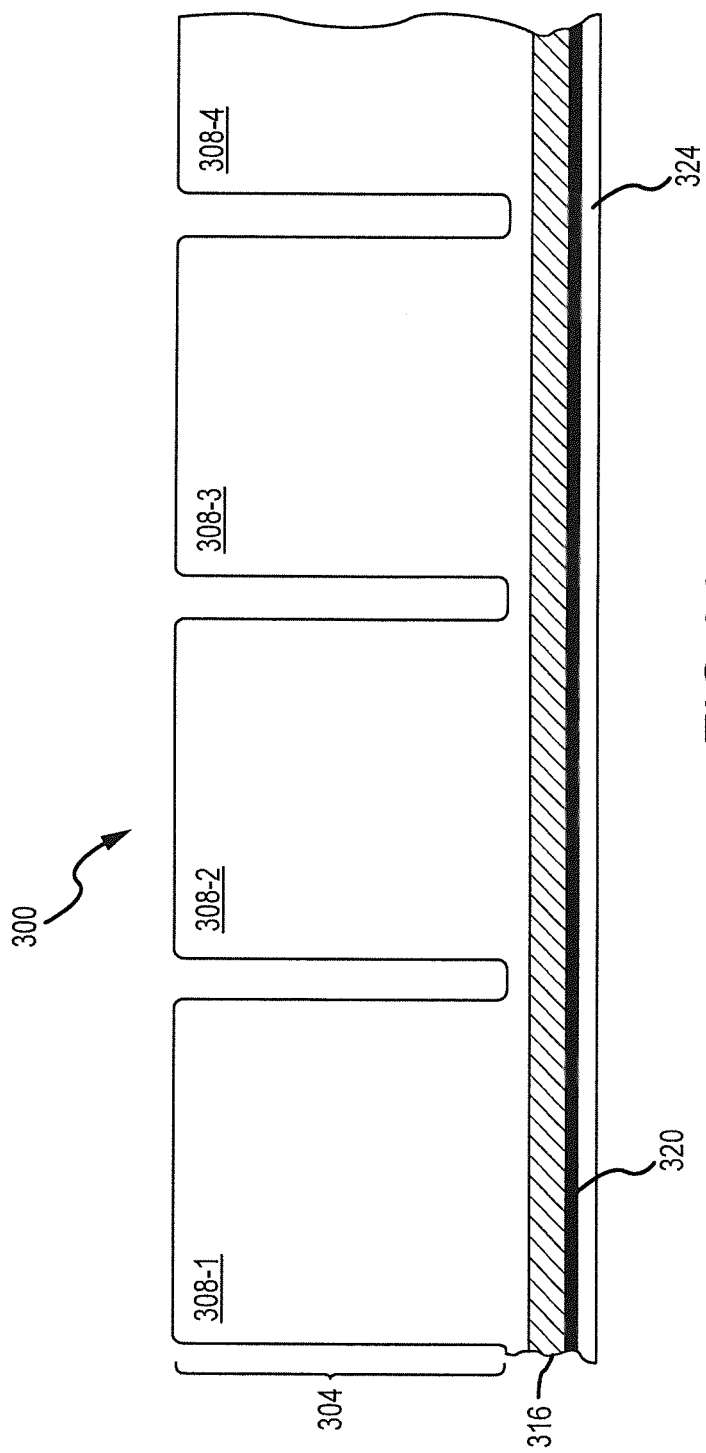

COOLING MEDICAL PAD

RELATED APPLICATIONS

This application claims priority to U.S. Provisional Patent Application No. 61/381,840, filed Sep. 10, 2010, entitled "COOLING MEDICAL PAD," and U.S. Provisional Patent Application No. 61/389,056, filed Oct. 1, 2010, entitled "COOLING MEDICAL PAD," both of which applications are incorporated herein by reference in their entirety.

FIELD OF THE INVENTION

The present invention relates to cooling medical patients. More specifically, this application relates to a cooling pad for treating medical patients benefiting from cooling treatment and to methods for using such a cooling pad.

BACKGROUND OF THE INVENTION

There are a number of medical conditions in which systemic cooling is an effective therapy. For example, rapid systemic cooling of stroke and head-trauma patients has significant therapeutic benefits. Stroke is a major cause of death and neurological disability, but recent research has suggested that even though a stroke victim's brain cells may lose their ability to function during the stroke, they do not necessarily die quickly. Brain damage resulting from a stroke may take hours to reach maximum effect. Neurological damage may be limited and the stroke victim's outcome improved if a cooling neuroprotectant therapy is applied during that timeframe.

Similar possibilities exist with the victims of trauma such as may result from vehicle crashes, falls, and the like. Such trauma may cause brain injury through mechanisms that have overlap with elements in the genesis of neurologic damage in stroke victims. Delayed secondary injury at the cellular level after the initial head trauma event is recognized as a major contributing factor to the ultimate tissue loss that occurs after brain injury.

Cooling therapy has been shown in a number of studies to confer neuroprotection in stroke victims and may hasten neurologic recovery. Such cooling therapy may be applied with the use of a medical cooling pad that is placed on the patient. For example, the pad might be placed on the patient's torso and fluid such as water or air circulated through the pad. Thermal energy is then exchanged between the patient and the circulated fluid so that when the temperature of the fluid is lower than the desired temperature of the patient, the patient is cooled.

SUMMARY OF THE INVENTION

Embodiments of the invention provide a medical pad that comprises a plurality of layers. A first layer of the medical pad is for containing a first thermal-exchange fluid circulatable therethrough (e.g., cooled fluid circulated via an interconnected pump/heat exchange unit). The medical pad is selectively positionable to contact a patient on a first side thereof, and is operable for thermal exchange between the circulatable first thermal-exchange fluid and a patient through a first side of the first layer and the first side of the medical pad. A second layer of the medical pad may be disposed on a second side of the first layer, opposite to the first side of the first layer. The second layer encloses a second thermal-exchange fluid.

The medical pad is operable for thermal exchange between the second thermal-exchange fluid and the patient through the first side of the medical pad. In some approaches the second thermal-exchange fluid may comprise a liquid having a freezing point of 0° C. or less. In turn, in such approaches, the second thermal-exchange fluid contained in the second layer may be chilled, e.g., to at least a semi-frozen state, prior to use. Additionally, in such approaches, the second thermal-exchange fluid may comprise liquid in a gel form. For example, a gel material comprising a water/polymer matrix may be utilized. In some implementations, shape-holding gels may be utilized.

The medical pad may be configured for different levels of thermal communication with the first and second thermal-exchange fluids in different embodiments. In some embodiments, for example, greater than 30% of an area of the medical pad in contact with the patient is in thermal communication with the first thermal-exchange fluid (e.g., located adjacent thereto), and in a specific embodiment, approximately 50% of the area of the medical pad in contact with the patient is in thermal communication with the first thermal-exchange fluid (e.g., located adjacent thereto). Similarly, in other embodiments, greater than 30% of an area of the medical pad in contact with the patient is in thermal communication with the second thermal-exchange fluid (e.g., located adjacent thereto), and in a specific embodiment, approximately 50% of the area of the medical pad in contact with the patient is in thermal communication with the second thermal-exchange fluid (e.g., located adjacent thereto).

In one embodiment, approximately 50% of the area of the medical pad in contact with the patient is in thermal communication with the first thermal-exchange fluid (e.g., located adjacent thereof) and approximately 50% of the area of the medical pad in contact with the patient is in thermal communication with the second thermal-exchange fluid (e.g., located adjacent thereto).

The second layer may extend across at least a majority of a lateral extent of the first layer. Further, the second layer may comprise a plurality of chambers. In some such embodiments, the plurality of chambers may each enclose a corresponding different portion of the second thermal-exchange fluid therewithin. In some embodiments, at least a portion of each of the plurality of enclosed chambers may be located laterally adjacent (e.g., side-by-side) with corresponding first thermal-exchange fluid containment portions, e.g., fluid flow channels, of the first layer.

Each of the plurality of chambers may project away from the second side of the first layer with indentations defined therebetween. For instance, the plurality of chambers may, in one embodiment, define a waffle-shaped configuration. The provision of indentations between adjacent chambers (e.g., laterally and/or longitudinally extending indentations), together with the utilization of pliable materials to define the first and second layers, allows for a degree of pivotal, or hinge-like movement, about such indentations. Such feature facilitates medical contact with a patient and is particularly advantageous when the second thermal-exchange fluid is in a solid or semi-solid state (e.g., ice).

An adhesive surface may be disposed on the first side of the first layer and adapted for releasable adhesive contact with skin of a patient. In certain embodiments, the adhesive surface extends across at least a majority of a lateral extent of the first layer. In such embodiments, the first and second layers may also be adapted for conformal contact between the adhesive surface and the skin of the patient. For example, as indicated above, the first and second layers may be defined by pliable materials.

Ports may be fluidly interconnected to the first layer for selective interconnection to a separate pump/heat exchanger unit provided for circulation of the first thermal-exchange fluid. In such cases, a first port is fluidly interconnected to the first layer for circulating the first thermal-exchange fluid into the first layer and a second port is fluidly interconnected to the first layer for circulating the first thermal-exchange fluid out of the first layer.

Embodiments of the invention may also comprise different thermal properties for the thermal-exchange fluids. For example, at least one of the first thermal-exchange fluid or the second thermal-exchange fluid may have a thermal conductivity that exceeds 5.0 W/mK, that exceeds 10.0 W/mK, that exceeds 50.0 W/mK, that exceeds 100.0 W/mK, or that exceeds 250 W/mK in various embodiments. The at least one of the first thermal-exchange fluid or the second thermal-exchange fluid may comprise a liquid containing a material having a thermal conductivity that exceeds a thermal conductivity of the liquid by at least a factor of 10, a factor of 50, a factor of 100, a factor of 500, or a factor of 1000 in various embodiments.

Embodiments of the invention also include methods for contact cooling of a patient and for providing a medical pad for contact cooling. In the former aspect, a medical pad may be positioned on a patient. Thermal energy is transferred as part of a first transferring step between a contained layer of the medical pad and the patient. The contained layer may enclose a first thermal-exchange fluid that is chilled, e.g., to a temperature of 5° C. or less (e.g., frozen water). Thermal energy is also transferred as part of a second transferring step between a circulation layer of the medical pad and the patient by circulating a second thermal-exchange fluid through the circulation layer of the medical pad.

The first transferring step may be performed over greater than 30% of an area of the medical pad in contact with the patient, and in some cases is performed over approximately 50% of an area of the medical pad in contact with the patient. Similarly, the second transferring step may be performed over greater than 30% of an area of the medical pad in contact with the patient, and in some cases is performed over approximately 50% of the area. In one embodiment, the first transferring step is performed over approximately 50% of an area in contact with the patient and the second transferring step is performed over approximately 50% of the area.

The first and second transferring steps may be at least partially offset. For instance, the first transferring step may be initiated at a first location and the second transferring step may be initiated at a second location different from the first location. In such cases, the patient may be moved from the first location to the second location between initiation of the first transferring step and initiation of the second transferring step, such as in an ambulatory vehicle. In some embodiments, at least a portion of the first transferring step is completed during the moving step.

The method may also comprise cooling the medical pad prior to each of the positioning, first transferring, and second transferring steps. In such cases, the first thermal-exchange fluid may be chilled by such cooling to a temperature below at least 5° C. In some approaches, the first thermal-exchange fluid may be chilled to a frozen or semi-frozen state prior to positioning at the pad on a patient.

In some embodiments, the medical pad may be positioned on the patient by adhering the medical pad to skin of a bodily portion of the patient. In such embodiments, a liner may be removed from an adhesive surface of the medical pad, and the adhesive surface of the medical pad may be contacted with the skin of the bodily portion of the patient. The adhesive surface may extend across at least a majority of a lateral extent of the circulation layer. Thermal exchange may occur across the adhesive surface during the first transferring step and during the second transferring step, e.g., without displacing or otherwise repositioning the medical pad relative to the patient.

In some embodiments, the second transferring step comprises fluidly interconnecting the medical pad to a fluid control system. In such embodiments, the second thermal-exchange fluid may be circulated through the circulation layer of the medical pad and the fluid control system.

Numerous additional features and advantages of the present invention will become apparent to those skilled in the art upon consideration of the embodiment descriptions provided hereinbelow.

BRIEF DESCRIPTION OF THE DRAWINGS

A further understanding of the nature and advantages of the present invention may be realized by reference to the remaining portions of the specification and the drawings wherein like reference numerals are used throughout the several drawings to refer to similar components. In some instances, a sublabel is associated with a reference numeral following a hyphen to denote one of multiple similar components. When reference is made to a reference numeral without specification to an existing sublabel, it is intended to refer to all such multiple similar components.

FIGS. 3A and 3B provide cross-sectional views of medical pads for different embodiments of the invention;

FIG. 10 is a bottom view of the layer of the medical pad embodiment of FIG. 8 that is shown in FIG. 10C.

DETAILED DESCRIPTION

Embodiments of the invention provide a medical pad and methods of contact cooling a patient. The medical pad includes a plurality of layers, at least one of which is a circulation layer for containing a circulatable thermal-exchange fluid that can circulate through the layer and at least one of which is a containment layer that encloses a contained thermal-exchange fluid.

Figure 1:
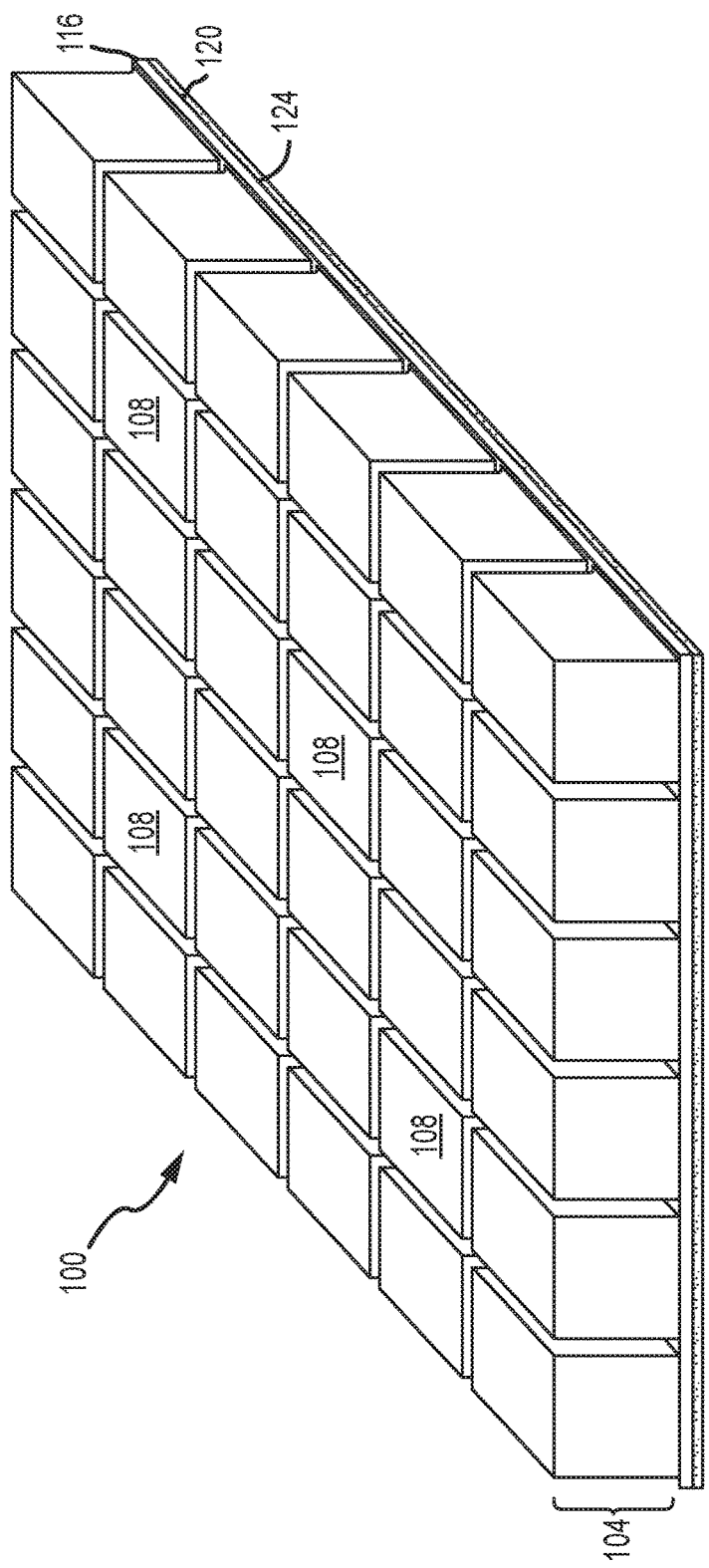
FIG. 1 illustrates a general configuration for a medical pad in accordance with embodiments of the invention.

A general overview of one structure for the medical pad according to embodiments of the invention is provided with FIG. 1, which shows a three-dimensional view of a portion of a medical pad 100. A circulation layer 116 comprises a fluid-containing layer for containing the circulatable thermal-exchange fluid that is capable of absorbing and/or releasing thermal energy. A circulation layer 116 may also comprise a conformable thermally conductive layer for facilitating thermal exchange with a patient.

An adhesive surface 120 may be disposed on a skin-contacting side of the circulation layer 116 for adhering the pad 100 to the skin of a patient. A removable liner 124 may be provided over the adhesive surface 120 to protect the adhesive surface 120 from contamination while the pad 100 is not in use. The removable liner 124 may be selectively removed when the pad 100 is used.

In one approach, the adhesive surface 120 may be provided as a number of downward-facing adhesive strips (e.g., peripheral strips and/or strips extending across the lateral extent of the medical pad), each having a selectively removable release liner 124 exposed thereupon. The adhesive strips may comprise a polyolefin or polyurethane film with hypoallergenic pressure-sensitive acrylate adhesive anchored to the pad 100 with a rubber-based pressure-sensitive adhesive.

In another approach, the adhesive surface 120 may be provided on a conformable, thermally conductive layer. The conformable, thermally conductive layer may comprise a first material, such as a liquid (e.g., water), suspended in a matrix defined by a second material, such as a polymer. In this regard, the liquid may preferably comprise between about 30 to 95 percent by weight of the total weight of the first and second materials. The adhesive surface and thermal transfer layers may be separately comprised of distinct materials. Alternatively, a thermally conductive layer may be comprised of a hydrogel material having sufficient adhesive properties so as to integrally provide the adhesive surface. In such approaches, the adhesive surface 120 may extend across the entirety or at least a majority of the skin-contacting side of medical pad 100.

A containment layer 104 may be interconnected with a second side of the circulation layer 116 that is opposite the skin-contacting side of the circulation layer 116. The containment layer 104 may include a plurality of chambers 108 which may be individually or collectively enclosed in some embodiments, or which may be enclosed in groups in other embodiments. Each of the chambers 108 may be defined by pliable members that project away from the second side of the circulation layer 110 and may have indentations therebetween as illustrated in the drawing (e.g., thereby defining a waffle-like configuration).

A first thermal-exchange fluid is generally used for circulation through the circulation layer 116 and a second thermal-exchange fluid is generally used for containment in the containment layer 104. As described in further detail below, the first and second thermal-exchange fluids may sometimes be the same fluid, but this is not a requirement of the invention and different thermal-exchange fluids may be used in the circulation and containment layers in different embodiments. In the later regard, in some embodiments, the second thermal-exchange fluid may comprise a liquid of a gel material, e.g., a shape-holding gel material.

Figure 2A:
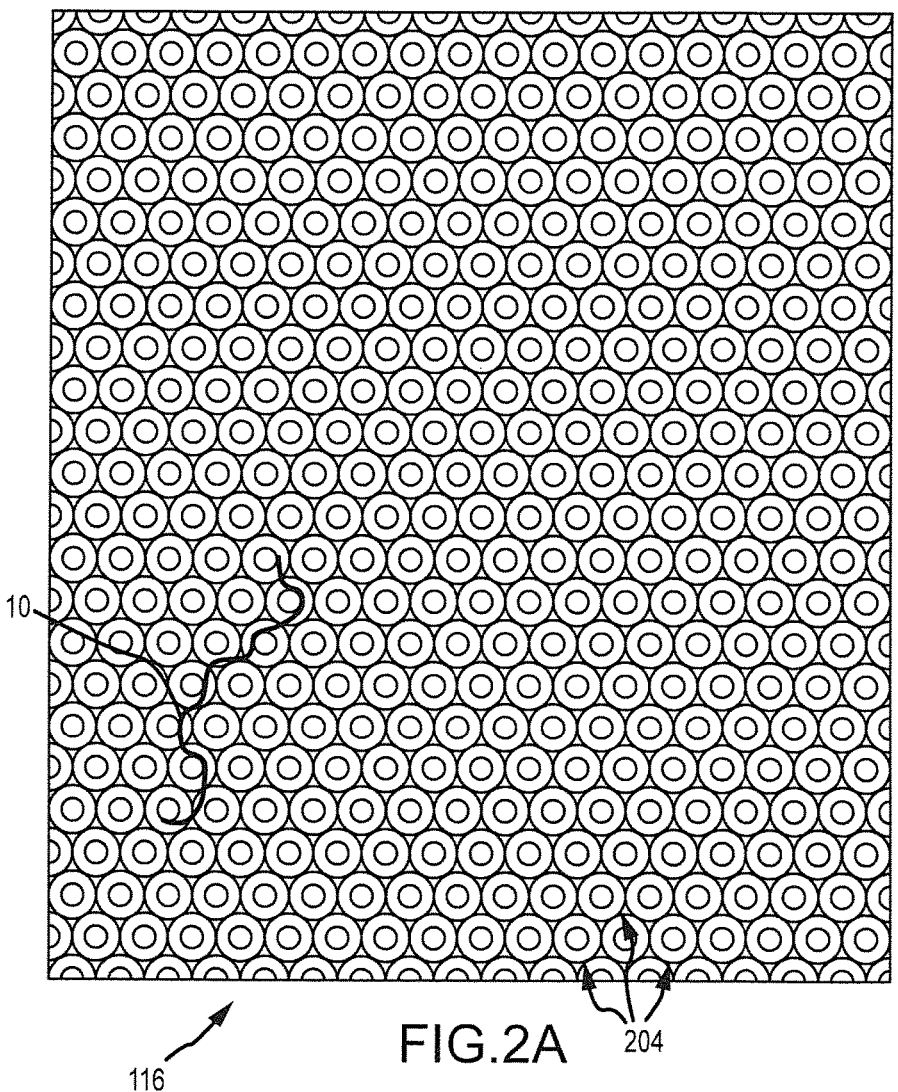
FIGS. 2A and 2B provide top and side views to illustrate a structure for a fluid-circulation layer of the medical pad in an embodiment.
Figure 2B:
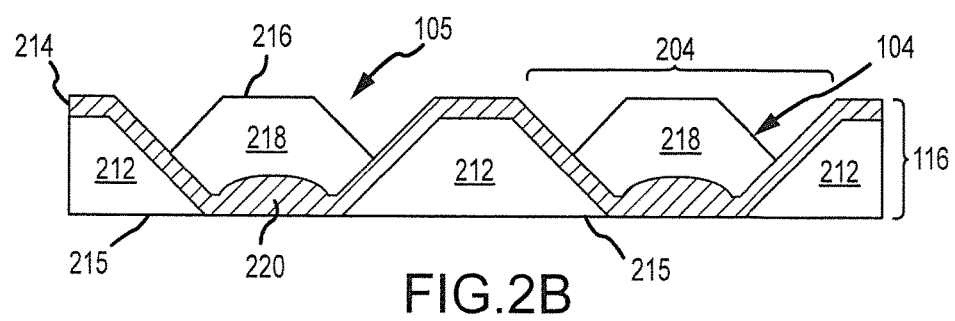

FIGS. 2A and 2B illustrate details of a structure of the circulation layer 116 in an exemplary embodiment with top and side views. The circulation layer 116 comprises a dimple-matrix having a plurality of dimples 204 structured to achieve a desired level of thermal communication with the thermal-exchange fluids in the circulation and containment layers. Fluid paths are provided within the circulation layer 116 by channels 212 formed by the structure of the circulation layer 116 between the dimples 204. This allows the first thermal-exchange fluid to flow in meandering, or tortuous, pathways around the dimples. The availability of multiple meandering paths advantageously allows the first thermal-exchange fluid to flow through the circulation layer 116 with wide coverage, enhancing thermal exchange with the patient's skin and increasing effectiveness of the cooling. An example of a portion of one potential path is illustrated with bold line 210.

The cross-sectional view of FIG. 2B illustrates more particularly how the structure of the dimple matrix defines the channels 212 in one particular embodiment, and how thermal exchange with both the first and second thermal-exchange fluids is achieved. Specifically, a structure 214 (e.g., comprising a polymer-based material) may define the dimple matrix with channels 212 sealably provided between the structure 214 and a sheet-like layer 215 (e.g., comprising a polymer based material). Thermal exchange occurs between the first thermal-exchange fluid and a patient's skin at locations defined by the channels 212 where the first thermal-exchange fluid is disposed adjacent to, and thereby in direct or near-direct thermal communication with the skin of the patient when the medical pad is applied.

Thermal exchange between the second thermal-exchange fluid and the patient's skin may occur between the channels 212, at those locations where structure 214 of the circulation layer 116 allows for the second thermal-exchange fluid to fill the dimples 204. In the illustrated embodiment, separate enclosed chambers 218 comprising the containment layer 104 may be defined by dimples 204 and overlying obtruded portions 216 to provide adjacent positioning and direct or near-direct thermal communication between the skin of the patient and the second thermal-exchange fluid in the containment layer 104. In various embodiments overlying obtruded portion 216 may be sized to each extend over a plurality of dimples 204 to define separate enclosed chambers for containing the second thermal-exchange fluid.

With the illustrated structure, approximately 50% of the skin-contacting side of the circulation layer 116 is provided adjacent to and thereby in direct or near-direct thermal communication with the circulation layer and approximately 50% of the skin-contacting side of the circulation layer 116 is provided adjacent to and thereby in direct or near-direct thermal communication with the containment layer. The structure may be varied in other embodiments to achieve different relative levels of thermal communication between the different layers. For example, in varying embodiments, greater than 20%, greater than 30%, greater than 40%, greater than 50%, greater than 60%, greater than 70%, or greater than 80% of the skin-contacting side of the circulation layer 116 is provided in direct or near-direct thermal communication with the first thermal-exchange fluid. In other embodiments, greater than 20%, greater than 30%, greater than 40%, greater than 50%, greater than 60%, greater than 70%, or greater than 80% of the skin-contacting side of the circulation layer 116 is provided in direct or near-direct thermal communication with the second thermal-exchange fluid.

It is noted that while the embodiment illustrated in FIGS. 2A and 2B generally provides approximately 100% of the skin-contacting side of the circulation layer 116 in communication with one or the other of the thermal-exchange fluids, this is also not a specific requirement of the invention. The total area of the skin-contacting side of the circulation layer 116 may at times have less than 100% of its area in communication with one of the thermal exchange layers. While there may be advantages in treating certain conditions to having 100% of the area in communication with a thermal-exchange fluid purely for treatment reasons, the many varying shapes of parts of the body where treatment may be applied may make it preferable to have configurations in which less than 100% of the area is in thermal communication in order to provide greater structural integrity to the medical pad for such applications, to configure specialized circulation paths for certain areas of the body, or for other reasons such as may be evident to those of skill in the art. In specific embodiments, greater than 50%, greater than 60%, greater than 70%, greater than 80%, or greater than 90% of the area of the skin-contacting side of the circulation layer 116 is provided in thermal communication with one or both of the first and second thermal-exchange fluids.

The level of thermal communication with the different thermal-exchange fluids may also be provided as desired with different configurations of the containment layer. This is illustrated through a comparison of FIG. 3A with FIG. 3B for particular embodiments.

In the drawing of FIG. 3A, the pad is identified generally by reference number 300, with the containment layer 304 having a plurality of chambers 308. The circulation layer 316 is covered on the skin-contacting side with an adhesive layer 320 and removable liner 324.

The drawing illustrates the plurality of chambers 308 extending in a direction along the page, but it will be understood that the chambers 308 may also extend in a direction orthogonal to the page. In a specific embodiment in which the chambers 308 are thus provided in a generally rectangular configuration and each have substantially the same size and shape, the containment layer 304 may thus have a waffle-shaped configuration, but this is not a requirement of the invention. In other embodiments, the sizes of the chambers 308 may differ and the chambers 308 may be organized in other than a rectangular configuration, particularly as might be suitable for application to specific portions of the body or for specialized applications.

In the embodiment of FIG. 3A, fluid in the containment layer 304 is provided in direct thermal communication with the circulation layer 316 so that the dimples 304 of the circulation layer may hold some of the second thermal-exchange fluid. This embodiment also allows the different chambers 304 of the containment layer 304 to be in fluidic communication with each other.

Figure 3B:
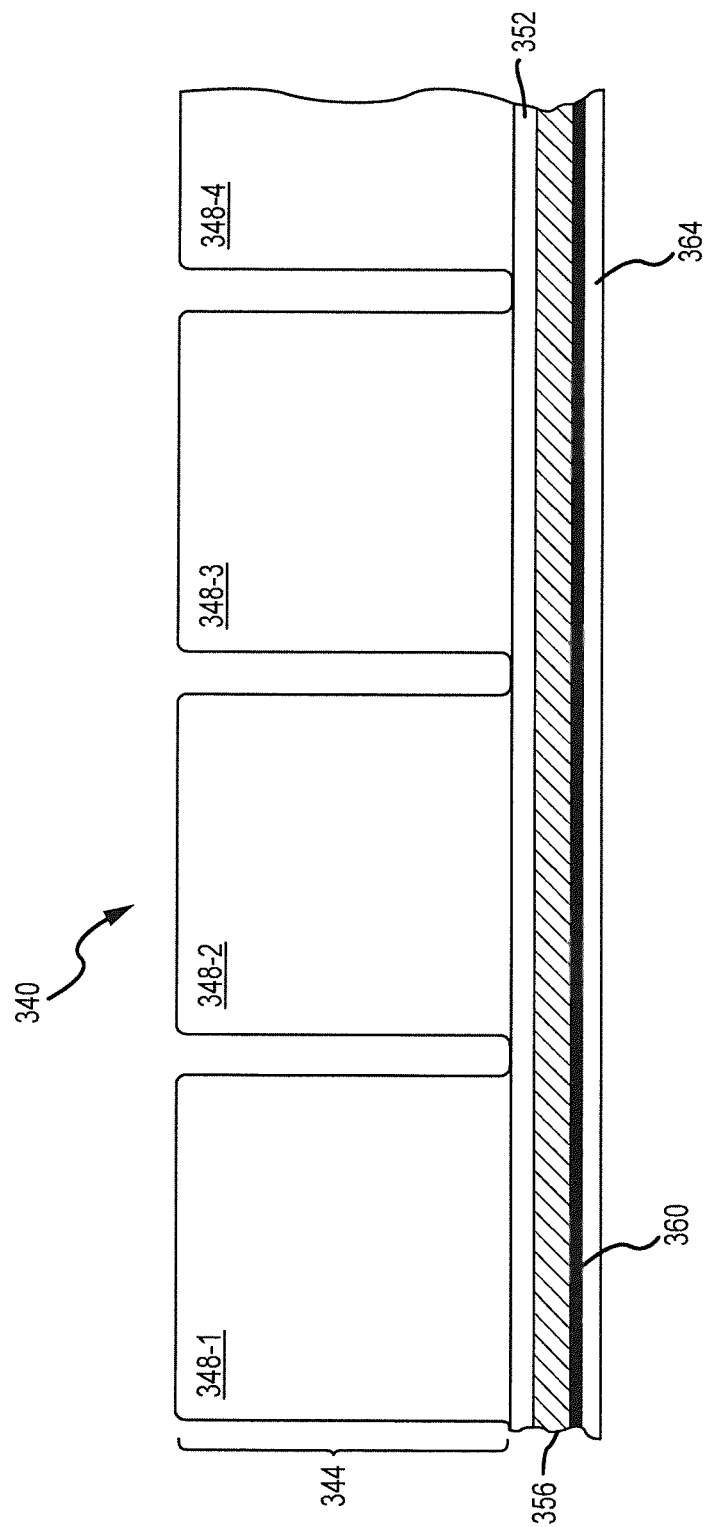

In an alternative embodiment such as illustrated in FIG. 3B, the medical pad 340 includes membrane 352 (e.g., a pliable layer of a polymer-based material) provided between the containment layer 344 and the circulation layer 356, which is also covered by an adhesive 360 on the skin-contacting side and a removable liner 364. The membrane acts to enclose the chambers 348 of the containment layer 344 separately from the circulation layer 356. Such enclosure may be provided in a way that allows fluid communication between the chambers 348 or in a way that prevents fluid communication between the chambers 348, allowing the different chambers individually to encapsulate different thermal-exchange fluids. In some configurations, each chamber 348 might be enclosed individually, although in other arrangements that make use of the membrane 352, the chambers 348 may be enclosed in groups so that fluid communication is provided among separate sets of chambers 348. Such embodiments may be suitable for certain specialized applications in which different thermal properties are desired at different positions of the medical pad.

A number of different thermal-exchange fluids may be used in different embodiments of the invention for both the first and the second thermal-exchange fluids, including gases and liquids such as water. As will be appreciated by those of skill in the art, the thermal-exchange characteristics of the pad 100 may depend on the thermal properties of the thermal-exchange fluids that are used. In particular, some embodiments make use of thermal-exchange fluids that include impurities, which may be in solid, liquid, or gaseous form, to tailor the thermal-exchange properties of the pad.

Table I indicates the thermal properties and densities of certain exemplary materials that may be used in different embodiments and of the thermal properties and densities of biological tissues that may interact thermally with the pad 100.

TABLE I

| Material | Heat Capacity (kJ/kg ° C.) | Thermal conductivity (W/mK) | Density (g/cm$^3$) |
| --- | --- | --- | --- |
| Aluminum | 0.9 | 230 | 2.71 |
| Graphite | 0.7 | 170-370 | 2.2 |
| Copper | 0.38 | 390 | 8.97 |
| Water | 4.186 | 0.57 | 1 |
| Ice | 2.1 | 1.7 | |
| Muscle tissue | 3.6 | 0.36-0.5 | 1 |
| Bone | 1.2 | 0.5 | 2 |
| Fat | 1.67 | 0.186-0.3 | 0.93 |
| Blood | 4 | 0.472-0.62 | 1 |

As noted in the table, a combination of water and a metal or other material such as those listed in the table may yield a greater thermal conductivity. If water is supplemented, for example, with 10 vol. % aluminum or graphite, its thermal conductivity increases by a factor of about 20. By mixing the substances in this way, the fluidic properties of water may advantageously be used while simultaneously increasing thermal conductivity. Although aluminum and graphite have similar thermal-conductivity, the specific-heat capacity of graphite offers additional advantages over the use of aluminum in some embodiments.

In one embodiment, a first thermal-exchange fluid may comprise a liquid such as water for circulation through the circulation layer 116. Further, the second thermal-exchange fluid may comprise liquid of a gel material. In one approach, a cellulose gel material may be utilized that is flowable into the containment layer 104 and curable to assume a shape-holding state within the containment layer 104. For example, a carboxmethyl cellulose (CMC) gel may be utilized that includes aluminum acetate to crosslink the CMC and form a shape-holding gel.

Figure 4:
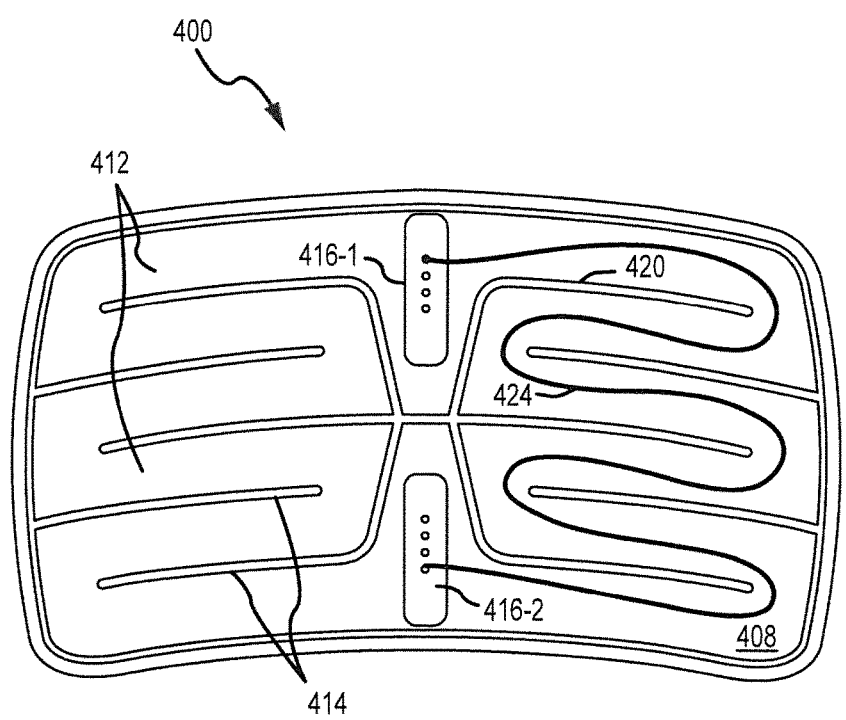
FIG. 4 illustrates an exemplary medical-pad structure for application to a patient in an illustrative embodiment.

FIG. 4 provides one illustration of a medical pad configuration 400 of a circulation layer, as described above, with the patient-facing layer thereof removed. As will be appreciated by those of skill in the art, there are many configurations that may be used depending on such factors as the part or parts of the body to which the medical pad is to be applied, the nature of the condition to be treated, the environment where the condition is to be treated, i.e., whether it is in a hospital, physician's office, accident site, or otherwise.

The configuration 400 includes areas 408 where dimples of the circulation layer (not shown) may be provided, e.g., as described above. Channels 412 may be defined by ribs 414, or raised portions. Fluid is circulated through the circulation layer through fluid ports that may be provided at manifold bonding sites 416 to provide access to the channels 412 within the circulation layer. The location, configuration, and orientation of the ports may be selectively established to provide various advantages. In particular, the ports may be provided to avoid patient weight from creating localized high-pressure areas on the skin by pressing the port or attached tubing against the skin of the patient. Reducing such high-pressure areas reduces the risk of causing pressure ulcers. Also, the tubing can exit off an a patient support platform (e.g., an emergency liter) without multiple turns, thereby reducing the risk of interconnected tubing buckling or kinking, which would limit fluid flow.

The ribs 414 prevent the first they mal-exchange fluid from following a path directly between the input and output ports of the circulation layer, e.g., going directly from site 416-1 to site 416-2. Instead, the first thermal-exchange fluid flows along a path such as illustrated with bold line 424. It is noted that this exemplary path is schematic; at a more detailed level, the actual paths followed by the first thermal-exchange fluid are meandering paths as dictated by the dimple structure of the layer and as explained above in connection with FIGS. 2A and 2B.

Specific configurations for the fluid channels may be as described in, for example, U.S. Pat. No. 6,648,905, the entire disclosure of which is incorporated herein by reference for all purposes. For instance, a first plurality of channels within the circulation layer may be of coincidental, serpentine configuration. More particularly, each of the channels comprising the first plurality of channels may be of a generally S-shaped configuration. Such channels may be of a substantially common length, such as in embodiments where each channel has a length within about 15% of an average length as measured along their respective center paths. Similarly, the channels may also have a substantially common average width, such as in embodiments where each channel has a width within about 25% of an average of the average widths of each channel. A second plurality of channels may also be disposed in a coincidental manner and similarly have substantially common lengths and widths as defined. The structure may also include fluid staging chambers at the fluid ports to distribute fluid and normalize fluid flow through the different pluralities of channels.

Figure 5:
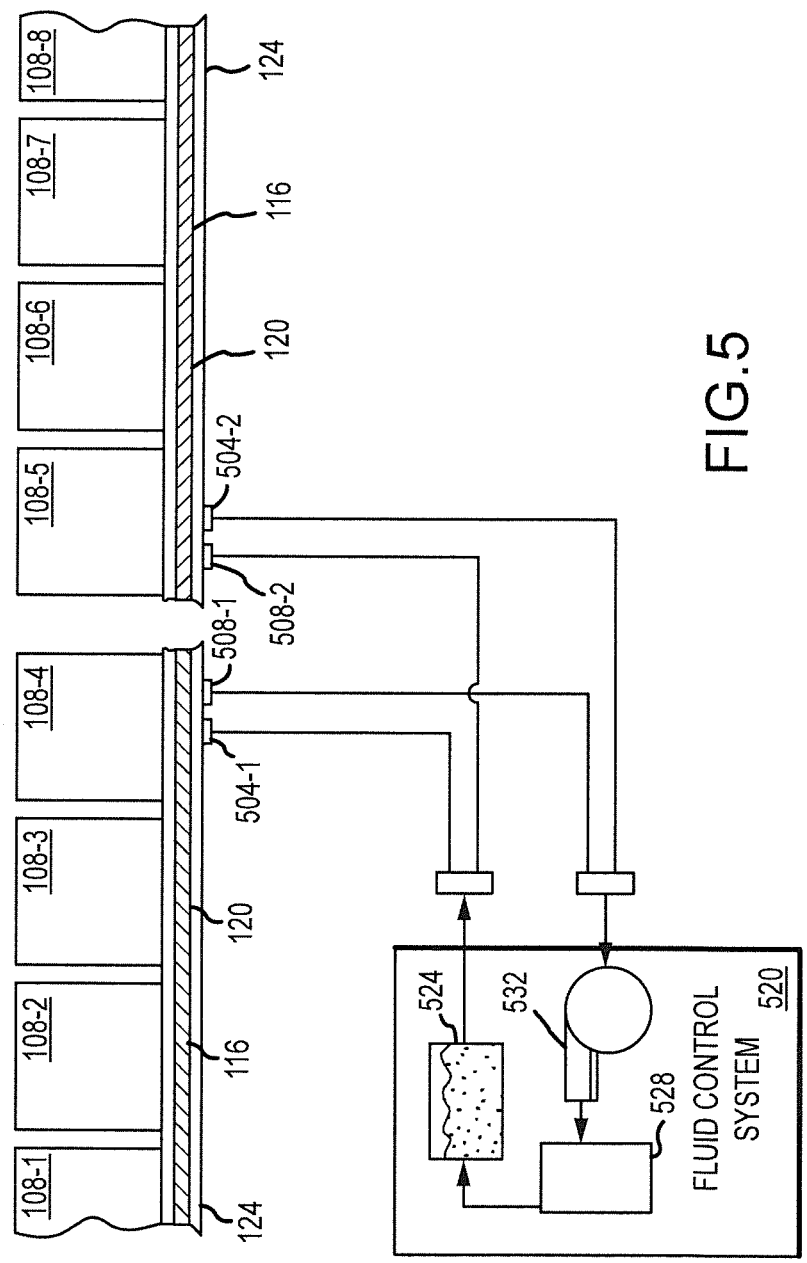
FIG. 5 provides a schematic illustration of a plurality of medical pads fluidly interconnected with a fluid control system.

FIG. 5 provides a schematic illustration of how circulation may be achieved through the circulation layer 116. The drawing shows a plurality of pads, such as may be appropriate for a configuration to be applied to various parts of the body where the shape of the body makes it less effective to use a single pad. For instance, application to the torso may involve the use of a pad 100 for the right side of the patient and a pad 100 for the front side of the body where it curves. Application to the legs might involve separate pads for each of the legs, etc. Each of the plurality of pads 100 is shown to have the same general structure as the pad 100 described in detail in connection with FIG. 1, including both a circulation layer 116 and a containment layer 104 having a plurality of chambers 108.

Fluid may be circulated through the fluid ports 504 and 508 by an interconnectable fluid-control system module 520, such as through interconnected tubing lines. In one arrangement, the fluid-control system module 520 comprises a pump 532 for drawing fluid through the pads 100 under negative pressure, usually less than about -10 psi, although other pressures may be used in different embodiments. At least one thermal-exchange device 528 is provided for cooling the circulated fluid and a fluid reservoir 524.

Figure 6:
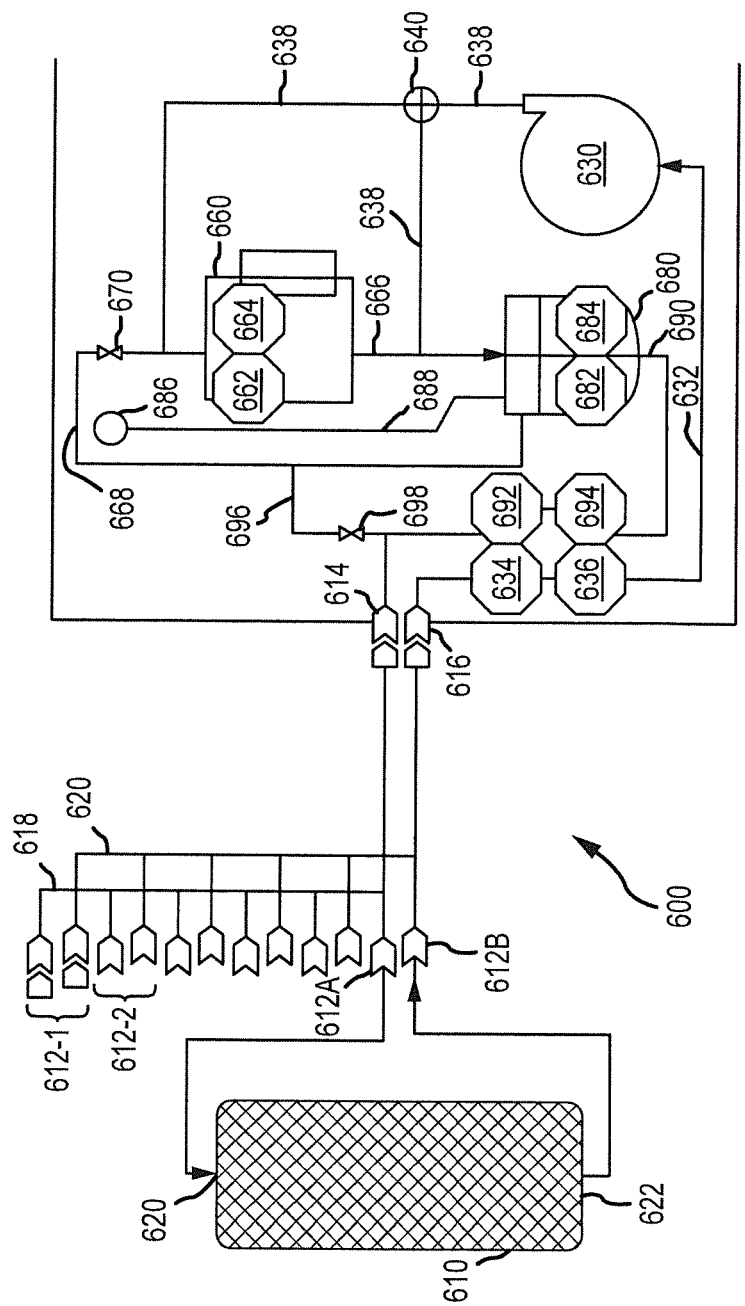
FIG. 6 is a fluid-circuit diagram illustrating on embodiment of a medical pad and related fluid-circulation system in accordance with an embodiment of the invention.

A fluidic circuit diagram is shown in FIG. 6 to illustrate in greater detail how fluid is circulated through the medical pad, designated by reference number 610 in the drawing. The medical pad is connected with the fluid circulating system 600 using pad-connector pairs 612. Each pad-connector pair 612 includes an inlet connector 612A for connection with an inlet 620 of the medical pad 610 and an outlet connector 612B for connection with an outlet 622 of the medical pad 610. Both the inlet and outlet connections may be made with flexible tubing or similar structure suitable for fluidic connection. Merely by way of illustration, the embodiment shown includes six pad-connector pairs 612 to permit connection of six medical pads 610 with the fluid circulating system 600. But it should be appreciated that the invention is not limited by the number of pad-connector pairs 612 and that different embodiments might have a greater or lesser number of pad-connector pairs 612. Each inlet connector 612A of the pad-connector pairs 612 is connected via an inlet feeder line 618 to a main inlet connector 614, and each outlet connector 612B of the pad-connector pairs 612 is connected via an outlet feeder line 620 to a main outlet connector 616. The fluid circulating system 600 also includes a pump 630, a temperature storage module 660, and a fluid reservoir 680.

The pump 630 is connected downstream via a pump inlet line 632 from the main outlet connector 616 and is preferably self-priming. A temperature sensor 634 and a pressure sensor 636 in the pump inlet line 632 measure the temperature and pressure respectively of the fluid exiting the pad 610 or pads connected with the fluid circulating system 600. Information from the pressure sensor 636 may be used in controlling the speed of the pump 630 so that generally constant negative pressure is maintained. The pump 630 is connected upstream via pump outlet lines 638 and a three-way valve 640 with both the reservoir 680 and the temperature storage module 660.

The temperature storage module 660 includes cooling elements 662 and a temperature sensor 664. The cooling elements 662 may be activated to cool fluid within the temperature storage module 660 to a desired temperature detectable by the temperature sensor 664. The temperature storage module 660 is connected via a primary temperature storage module outlet line 666 upstream from the reservoir 680 so that fluid that has been cooled to a desired temperature within the temperature storage module 660 flows therefrom to the reservoir 680 while the pump 630 is operating, i.e., pumping fluid therethrough. The three-way valve 640 may be regulated to control the proportion of fluid that flows to the reservoir 680 directly from the pump 630 and the portion of fluid that flows from the pump 630 through the temperature storage module 660 to the reservoir 680 in order to control the temperature of the fluid flowing into the pad 610. The temperature storage module 660 is also connected via a secondary temperature storage module outlet line 668 to the reservoir 680. A normally open valve 670 in the secondary temperature storage module outlet line 668 permits fluid to drain from the temperature storage module 660 to the reservoir 680 when the pump 630 is not operating.

The fluid reservoir 680 includes a level sensor 682 for detecting a level of fluid within the reservoir 680 and cooling element 684 for precooling fluid within the reservoir 680. When desirable, such as when the level sensor 682 indicates that the fluid level has fallen below a specified level, additional fluid may be added to the reservoir through a fill port 686 that is connected with the reservoir 680 by a fill line 688. Preferably, the reservoir 680 has a nonmixing inlet and outlet in order to minimize undesirable temperature variations of fluid within the reservoir. The outlet of the reservoir 680 is connected via a reservoir outlet line 690 to the main inlet connector 614. A temperature sensor 692 and a flow sensor 694 may be provided in the reservoir outline 690. The temperature sensor 692 measures the temperature of fluid provided to the pad inlets via the inlet feeder line 618. Information from the temperature sensor 692 may be used in regulating the three-way valve 640 to control the fluid temperature. Information from the flow sensor 694 and the temperature sensor 634 in the pump inlet line 632 may be used in determining the heat transfer between the patient and pads connected to the fluid circulating system 600. A drain line 696 with a normally closed two-way valve 698 is provided for draining the pads to the reservoir 680 when the cooling procedure is complete.

Other configurations may be used for the fluid circulating system 600 in alternative embodiments, examples of which are illustrated and described in commonly assigned U.S. Pat. No. 6,197,045, the entire disclosure of which is incorporated herein by reference for all purposes.

Figure 7:
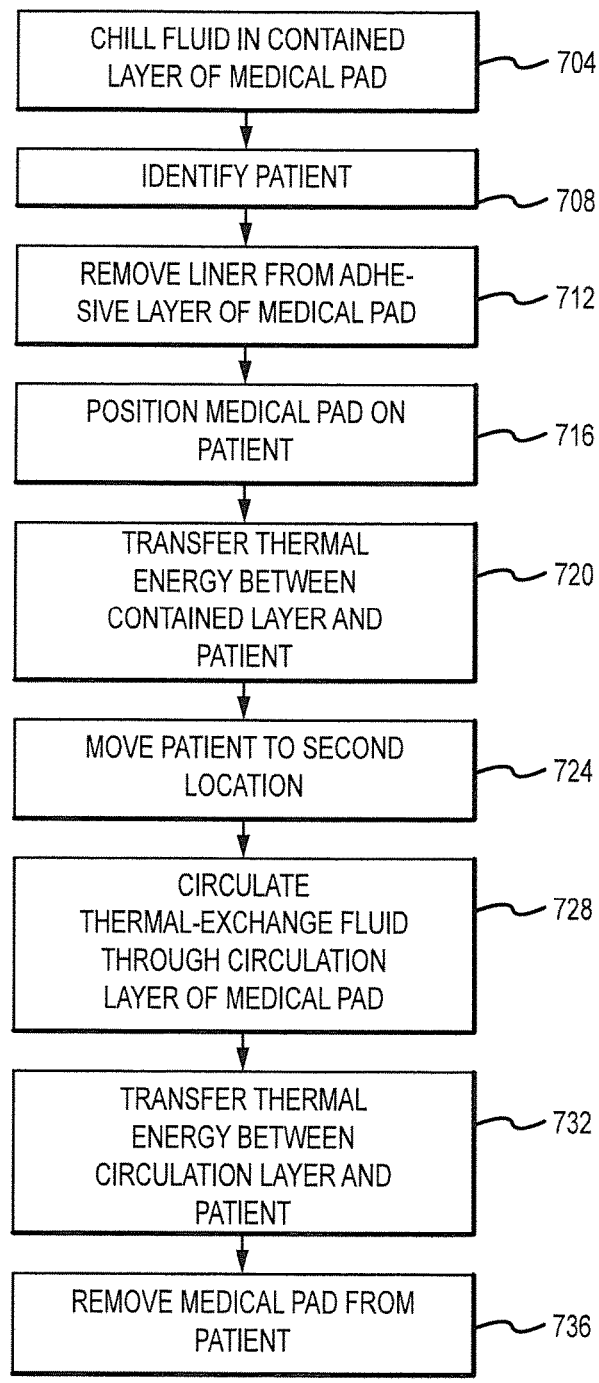
FIG. 7 is a flow diagram summarizing methods of using a medical pad in accordance with embodiments of the invention.

FIG. 7 provides a flow diagram that illustrates methods for using a medical pad in accordance with embodiments of the invention. While the flow diagram sets for specific functions that are performed and illustrates them in an exemplary order, these are not intended to be limiting. In various alternative embodiments, some of the functions may be omitted, others not specifically illustrated may additionally be performed, and/or the order may be changed from that illustrated specifically in the drawing.

The method begins at block 704 by chilling the second thermal-exchange fluid in the containment layer of the medical pad. As previously noted, different thermal-exchange fluids may be used in different embodiments and therefore the phase-transition points of the fluid may differ in different embodiments. In some embodiments, the second thermal-exchange fluid has a freezing point equal to or less than 0° C. In those embodiments where the second thermal-exchange fluid comprises water mixed with another substance, the freezing point may be higher or lower than 0° C. In certain embodiments, the second thermal-exchange fluid may comprise a liquid such as water comprising a shape-holding gel material that may be chilled to 0° C. or less, such that the liquid is in a frozen state or at least a partially frozen state at block 704, and wherein the shape-holding gel maintains an initial configuration as the second thermal-exchange fluid warms during use.

It is also noted that chilling the second thermal-exchange fluid at block 704 may or may not involve a phase change in the fluid. For example, if the second thermal-exchange fluid is pure water, it may be chilled to a temperature on either side of its freezing point of 0° C. without deviating from the intended scope of the invention. Indeed, even if the second thermal-exchange fluid is frozen as part of the chilling at block 704, it is still considered to be a "fluid" as the term is used herein. Further, if the second thermal-exchange fluid has an evaporation point that is crossed as part of the chilling at block 704 so that it changes phase from a gas to a liquid, it is still considered to be a "fluid" as the term is used herein.

Use of the medical pad is generally expected to result in the transfer of thermal energy to the second thermal-exchange fluid, and such transfer may result in reversal of a phase change that occurs as part of the chilling at block 704. Such embodiments are also specifically intended to be within the scope of the invention.

At block 708, a patient is identified who is expected to benefit from application of a cooling therapy. The patient may be suffering from a stroke, head trauma, or other injury or disease that may be effectively treated with cooling therapy. It is specifically noted, though, that it is not a requirement of the invention that the patient be suffering from any type of disorder, whether it be an injury-caused disorder or otherwise. In some embodiments, the cooling therapy may be used as an adjunct to the application of other medical procedures, such as where a patient undergoing surgery is identified as likely to benefit from the application of cooling therapy.

The medical pad is applied to the identified patient at blocks 712 by removing a liner or plurality of liners from the adhesive layer, depending on whether the embodiments use a generally continuous adhesive layer or have a plurality of adhesive strips. In embodiments where no adhesive is used, block 712 may be omitted. At block 716, the medical pad is positioned on the patient. It is generally expected that the pad will be placed in contact with skin tissue with the adhesive being used to adhere the pad to the skin and thereby generally maintain its position on the patient during the cooling therapy. But in alternative embodiments, the pad may be positioned on other types of tissue, although such embodiments may omit the use of an adhesive.

The nature of the medical pad as described above, particularly its thermal properties, allows a transfer of thermal energy between the contained layer and the patient at block 720. The transfer results in cooling of the patient, at least locally in the area where the pad is applied and with consequent heating of the second thermal-exchange fluid.

At block 724, the patient is moved to a second location where the first thermal-exchange fluid may be circulated through the circulation layer of the medical pad at block 728. This results in thermal energy being transferred between the circulation layer and the patient at block 732. To realize fluid circulation, the medical pad may be selectively interconnected to a fluid control system. Circulation of the first thermal-exchange fluid may be achieved using the fluid control system as described in connection with FIGS. 5 and 6 and as also described in commonly assigned U.S. Pat. Nos. 6,197,045, 6,648,905, and 6,799,063, all of which are incorporated herein by reference in their entireties.

Movement of the patient at block 724 may take place in a number of different ways that reflect a variety of implementations of the invention. Such movement also combines with other aspects of the invention, particularly including the use of two thermal-exchange fluids that are used differently, to achieve numerous benefits. For example, there may be circumstances in which an appropriate fluid-control system is not available at the location where the medical pad is applied to the patient at block 716. This may occur, for instance, in emergency settings where a medical pad of the type described herein is maintained in an ambulatory vehicle for access by paramedics who do not have access to the fluid-control system at the emergency site. It may also occur in settings where a physician maintains medical pads of the type described herein at his or her office, but where the fluid-control system is maintained at a hospital. Still other settings where such circumstances may exist include clinics or nurses' offices in schools, which might maintain medical pads for use, but which lack the larger and more specialized fluid-control system equipment.

Irrespective of the particular circumstances, the combination of a containment layer and a circulation layer in a single medical pad provides a number of benefits in the treatment of conditions where cooling therapy is of value. While medical pads that include a circulation layer can provide effective cooling, the lack of ready availability of a fluid-control system at the site where the patient is first encountered risks losing time that may be critically important in preventing biological damage that could be mitigated with cooling therapy. Mere application of a cool substance such as ice is less effective for many reasons. As noted above, the second thermal-exchange fluid may be a substance that is better adapted for thermal exchange by having thermal-exchange properties that are more effective. Medical pads that include an adhesive also aid in maintaining a constant position on the patient for application of the cooling therapy. In addition, the integrated medical pad is already prepared in position on the patient for use with a fluid-control system when a location has been reached where such usage is possible. Timing for application of the cooling therapy can be critical in achieving the benefits of the therapy and the combination described herein can decisively make a difference in the level of irreversible biological damage that occurs to the patient, even preventing irreversible damage entirely in some cases.

Once the treatment has been applied, the medical pad may be removed from the patient at block 736. In conjunction with such removal, the medical pad may be disconnected from the fluid control system and disposed of.

Figure 8:
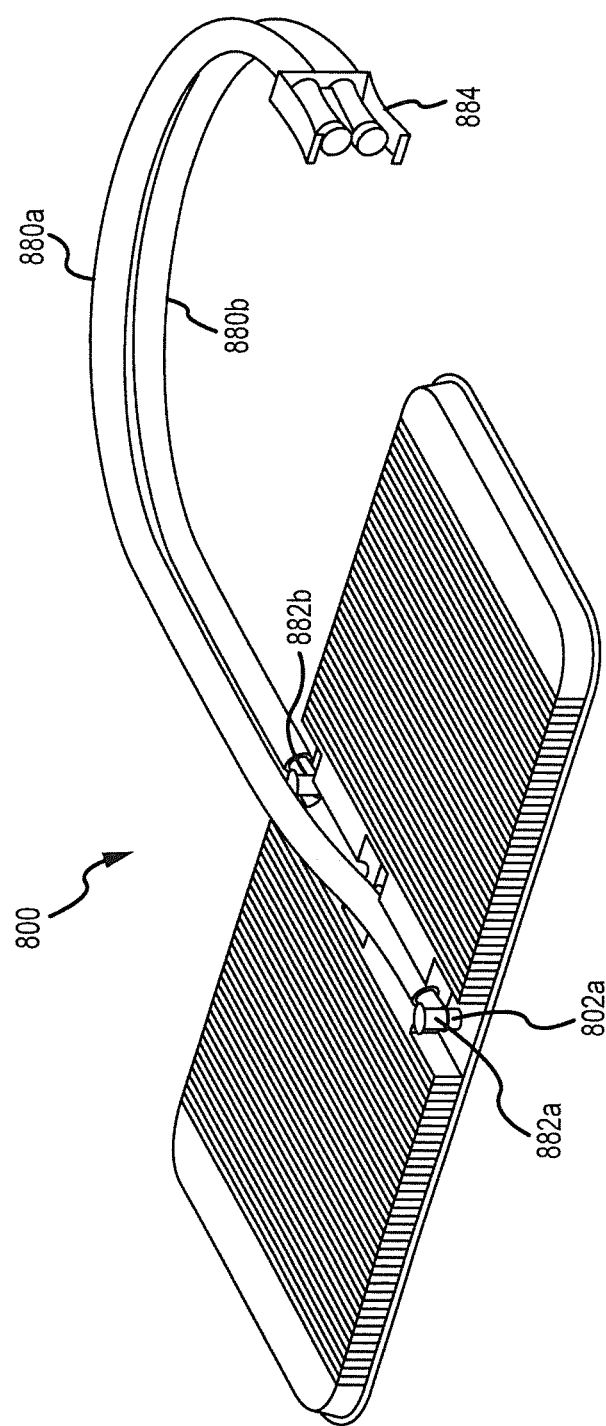
FIG. 8 illustrates another configuration of a medical pad embodiment.
Figure 9:
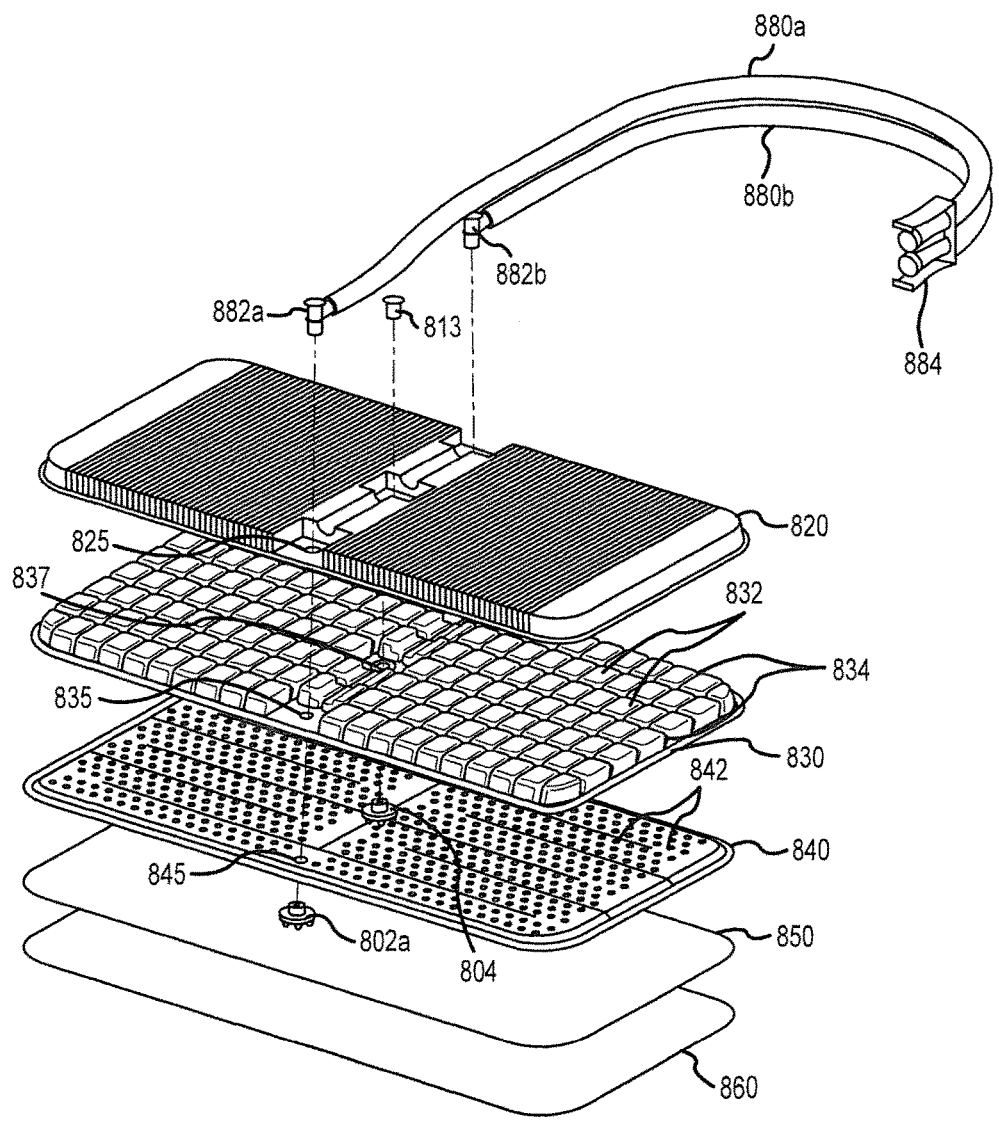
FIG. 9 is an exploded assembly view of the medical pad embodiment of FIG. 8.

FIGS. 8-13A and 13B illustrate another embodiment of a medical pad 800. As shown in FIGS. 8 and 9, fluid circulation lines 880*a*, 880*b* may be provided to circulate a first fluid thermal-exchange through the medical pad 800. For example, a connector 882*a* provided at a first end of fluid circulation line 880*a* may be fluidly interconnectable to a fluid inlet port 802*a* of medical pad 800, and a connector 882*b* provided at a first end of fluid circulation line 880*b* may be fluidly interconnectable to a fluid outlet port 802*b* of medical pad 800. Second ends of fluid circulation lines 880*a*, 880*b* may be provided for selective interconnection to and disconnection from a fluid control system of a type referenced hereinabove. In the illustrated embodiment, a connector device 884 may be provided at the second ends of the first and second fluid circulation lines 880*a*, 880*b* for interconnection with the fluid control system. In one approach, connector device 884 may be of a type described in U.S. Pat. No. 6,827,728.

Reference is now made to FIG. 9 which further illustrates medical pad 800. In the illustrated embodiment, medical pad 800 may include a top layer 820, a containment layer 830, an intermediate layer 840, an interface layer 850, and a bottom layer 860. As illustrated, the various layers may be arranged in a stacked, or laminate, fashion, and may be of a substantially common configuration (e.g., rectangular). In the later regard, various additional configurations are envisioned, including configurations designed for specific anatomic regions of use.

The intermediate layer 840 and interface layer 850 may be provided to define a circulation layer therebetween, wherein a first thermal-exchange fluid may flow into and out of such circulation layer via fluid circulation lines 880*a*, 880*b*.

Further, the intermediate layer 840 and containment layer 830 may be provided to define a containment layer therebetween for containing a second thermal-exchange fluid.

As will be appreciated, a second thermal-exchange fluid contained in the containment layer may be provided to cool a patient, independent from and/or in overlapping relation with the circulation of a first thermal-exchange fluid through the fluid circulation layer. Further, a first thermal-exchange fluid may be circulated through the fluid circulation layer to cool a patient, independent from and/or in overlapping relation with the patient cooling by a second thermal-exchange fluid contained within the containment layer.

In one approach, adjacent ones of the top layer 820, containment layer 830 and intermediate layer 840 may be interconnected about the peripheries thereof (e.g., via RF welding of copolymer materials comprising such layers). The interface layer 850 may be connected across a top side thereof to a bottom side of intermediate layer 840. The interface layer 850 may define an adhesive surface on a bottom side thereof for patient contact. In one approach, the fluid interface layer 850 may comprise a hydrogel material for presentation of an adhesive surface across the lateral extent of the bottom side of fluid interface layer 850 (e.g., across all or substantially all of the bottom side). For example, hydrogel materials may be utilized that comprise a polymer/water matrix marketed by AquaMed Technologies of Langhorne, Pa., U.S.A. The bottom layer 860 may comprise a removable liner, wherein the bottom layer 860 may be readily removed from the bottom adhesive surface of the interface layer 850 at the time of placement of medical pad 800 on a given patient for contact cooling (e.g., direct adhesive engagement with the skin of a patient). The adhesive surface may display a peel value at initial skin application of about 20 g/in. to 80 g/in. to facilitate fixed positioning on a patient, yet facilitate removal after use.

As illustrated in FIG. 9, the containment layer 830 may comprise a plurality of chambers 832 that project upward and away from a bottom side of the containment layer and upward from a top side of the intermediate layer, with indentations 834 between such chambers 832. A top side of the intermediate layer 840 may be provided with a plurality of depressions 842, e.g., a dimple-matrix, extending across the lateral extent thereof. In one approach, the chambers 832 and depressions 842 may be disposed in opposed, face-to-face relation for fluid communication therebetween, e.g., as shown in FIG. 13B below. In this regard, at least a portion of a second thermal-exchange fluid contained by the containment layer may be contained by the plurality of depressions 842 and the plurality of chambers 832 defining the containment layer.

In one approach, the chambers 832 and indentations 834 may be arranged in rows and columns to facilitate flexure of the medical pad along the indentations 834 for conformal engagement of medical pad 800 with a patient. In this regard, each of the layers 820, 830, 840 and 850 may be of a pliable construction to facilitate curvature, or flexure, along the lateral and/or longitudinal dimensions thereof By way of example, each of the layers may comprise a copolymer material such as a polyolefin material (e.g., ethylene-vinyl acetate).

Top layer 820 may be provided to define an insulative layer, or air space, between the top layer 820 and containment layer 830. In this regard, such insulative layer may surround chambers 832 to enhance thermal exchange between the second thermal-exchange fluid and a patient during use.

To further facilitate conformal positioning of medical pad 800 and/or enhanced thermal transfer between a patient and a first thermal-exchange fluid circulated through the circulation layer, the depressions 842 may be arranged in staggered rows and columns. In this regard, the depressions 834 on the top side of intermediate layer 840 provide corresponding projections on the bottom side of intermediate layer 840. In turn, tortuous flow paths around the projections may be defined within the fluid circulation layer.

Figure 10A:
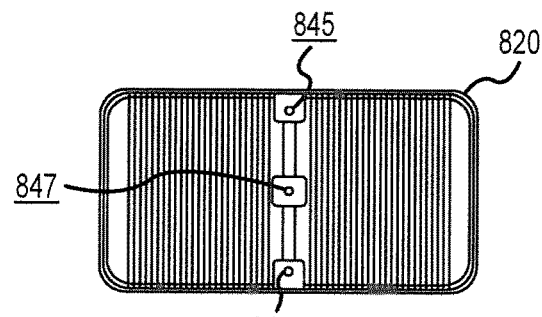
FIGS. 10A, 10B, 10C and 10D are top views of adjacent layers comprising the medical pad embodiment of FIG. 9.
Figure 10B:
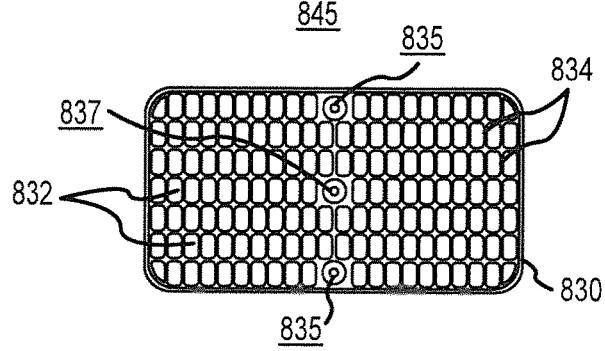
Figure 10C:
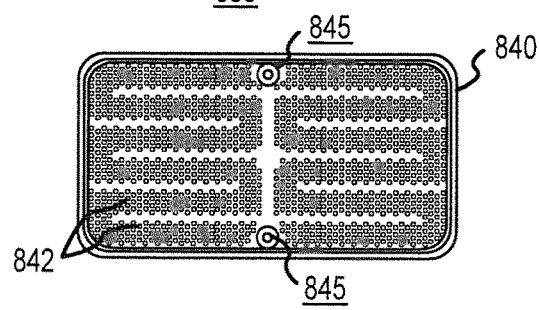
Figure 10D:
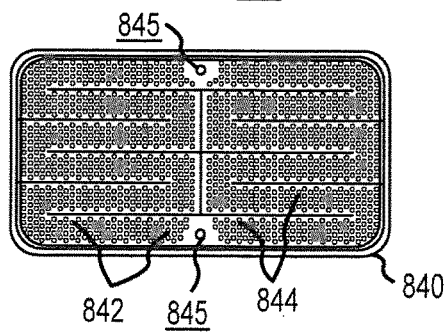

In relation to the above-noted features, reference is now also made to FIGS. 10A, 10B and 10C, which illustrate top views of layers 820, 830 and 840, and FIG. 10D which illustrates a bottom view of layer 840. Top layer 820 may define widthwise pleats, different ones of which may be positionable between columns of chambers 832 of containment layer 830. Top layer 820 may also include openings 825 for positioning of inlet port 802*a* and outlet port 802*b* therethrough.

As may be appreciated, the inlet port 802*a* and outlet port 802*b* may extend through aligned openings in the top layer 820, containment layer 830, and intermediate layer 840 to provide fluid communication with the circulation layer defined by intermediate layer 840 and fluid interface layer 850. Further, top layer 820 may include one or more opening(s) 827 for receipt of a fill port 804 therethrough, as shown in FIG. 9, for selective use in flowing a second thermal-exchange fluid into the containment layer (e.g., during assembly of medical pad 800). Reference is now made to FIG. 10B which illustrates containment layer 830 with chambers 832 and indentations 834 defining a matrix of rows and columns. Further, containment layer 830 may include openings 835 for positioning inlet port 802*a* and outlet port 802*b* therethrough. Additionally, containment layer 830 may include one or more opening(s) 837 for receipt of fill port 804 therethrough, as shown in FIG. 9. As illustrated in FIGS. 10C and 10D, intermediate layer 840 may also include openings 845 for positioning inlet port 802*a* and outlet port 802*b* therethrough. Additionally, intermediate layer 840 may include one or more opening(s) 847 for receipt of fill port 804 therethrough, as shown in FIG. 9.

In relation to FIG. 10C, depressions 842 are shown on the top side of the intermediate layer 840. In relation to FIG. 10D, such depressions 842 define downward projections on the bottom side of the intermediate layer 840. Additionally, ribs 844 are provided that project downward on the bottom side of the intermediate layer 840. In turn, tortuous flow paths may be defined for the flow of a first thermal-exchange fluid between ribs 844, around the projections defined by depressions 842. As may be appreciated, such tortuous fluid flow may occur between inlet port 802*a* and outlet port 802*b*.

Figure 11A:
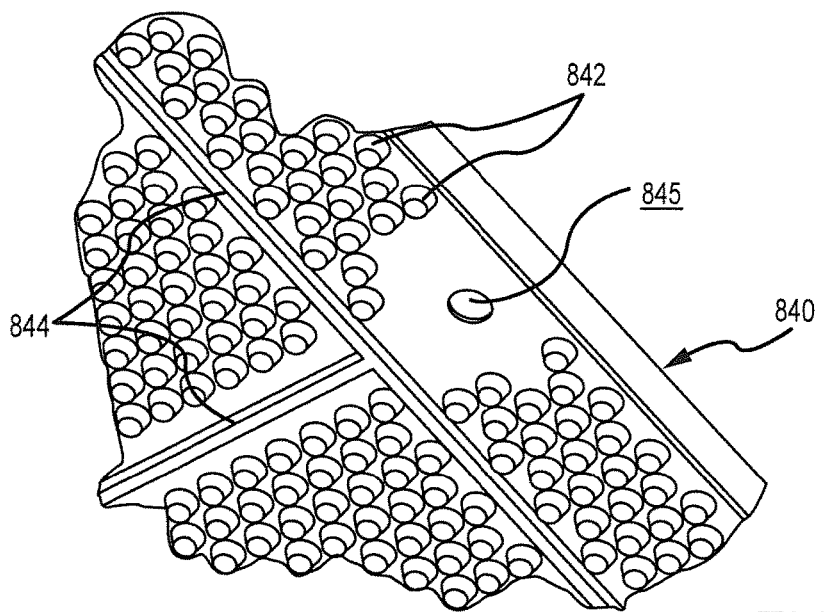
FIGS. 11A and 11B are bottom views of a cut-away, side portion of the layer of the medical pad embodiment of FIG. 8 that is shown in FIGS. 10C and 10D.

In this regard, reference is now made to FIGS. 11A and 11B, and FIGS. 12A and 12B. FIG. 11A illustrates a cutaway portion of a bottom side a side edge portion of intermediate layer 840, showing an opening 845 extending therethrough, and illustrating projections, corresponding with depressions 842 and ribs 844 projecting downward on the bottom side of the intermediate layer 840. As shown, depressions 842 are of an inverted, frusto-conical configuration.

Figure 11B:
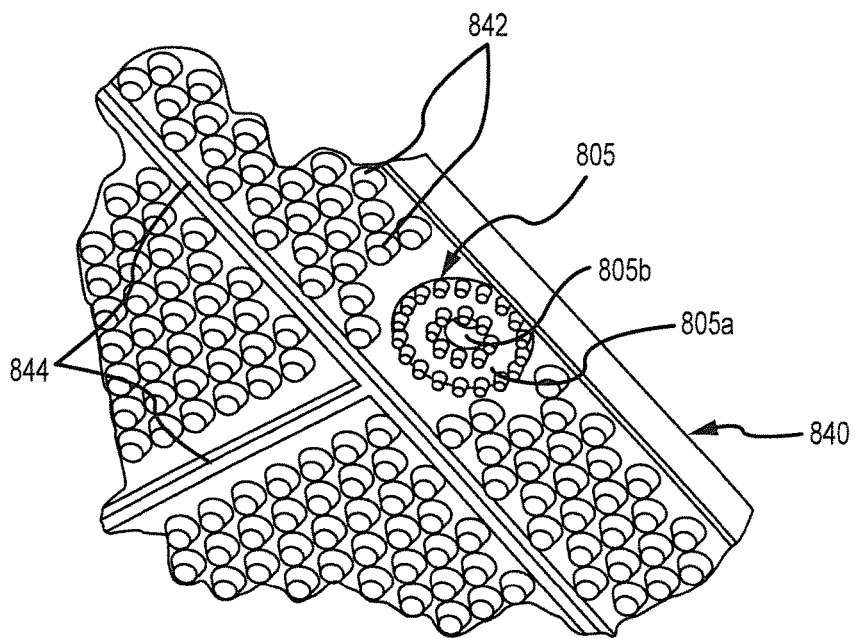

FIG. 11B illustrates the cutaway portion shown in FIG. 11A with an enlarged end 805 of inlet port 802*a* disposed on a bottom side of intermediate layer 840. As shown, enlarged end 805 includes a disk portion 805*a*, an aperture 805*b* and stand-off members 805*c* projecting away from disk portion 805*a* about aperture 805*b*. Inlet port 802*a* may be of a sufficiently rigid construction (e.g., comprising an integral, molded plastic material), such that stand-off members 805*c* maintain a desired layer-to-layer spacing for fluid flow at aperture 805*b*.

Figure 12A:
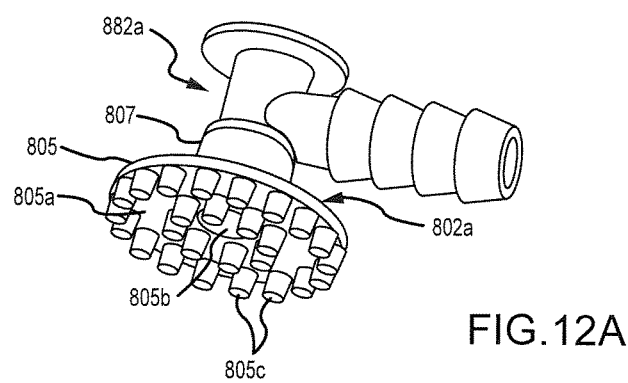
FIGS. 12A and 12B comprise a perspective view, and a cross-sectional perspective view, respectively, of an inlet port of the medical pad embodiment shown in FIG. 8 interconnected to a connector of a fluid circulation line illustrated in FIG. 8.
Figure 12B:
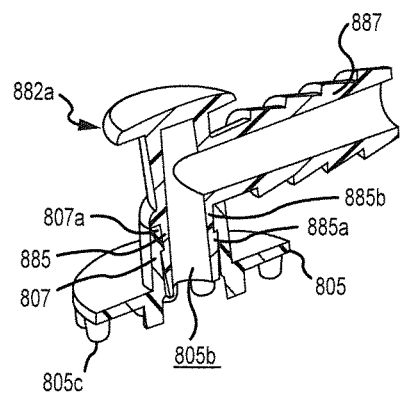

Inlet port 802*a* is shown interconnected to a connector 882*a* in FIGS. 12A and 12B. As illustrated, in addition to the enlarged end 805, inlet port 802*a* comprises a tubular portion 807 in fluid communication with aperture 805*b*. As may be appreciated, tubular portion 807 may be sized to fit through openings 825, 835, and 845 of the top layer 820, containment layer 830, and intermediate layer 840, respectively. Further, tubular portion 807 may be configured for selective interconnection with connector 882*a*.

For example, and as shown in FIG. 12B, tubular portion 807 may be configured together with connector 882*a* for one-way, snap-fit interconnection. For such purposes, a top end of tubular portion 807 may be sized to receive a tubular port 885 at connector 882*a*. Further, tubular portion may be provided with an inwardly protruding lip 807*a*. In turn, first tubular port 885 may have a tapered end portion 885*a* and adjacent recess 885*b* for snap-fit receipt of the lip 807*a* of the tubular portion 807 of the inlet port 802*a*. As further shown in FIGS. 12A and 12B, connector 882*a* may be of an L-shaped configuration that includes first and second tubular ports 885 and 887, adjoined at elbow 886, thereby yielding a low-profile interconnection footprint. Tubular part 887 may be barbed for retentive, fluid-type interconnection with tubing comprising fluid circulation line 880*a*. As may be appreciated, outlet port 802*b* and connector 882*b* may be configured in a manner analogous to inlet port 802*a* and connector 882*a* described above, respectively.

Figure 13A:
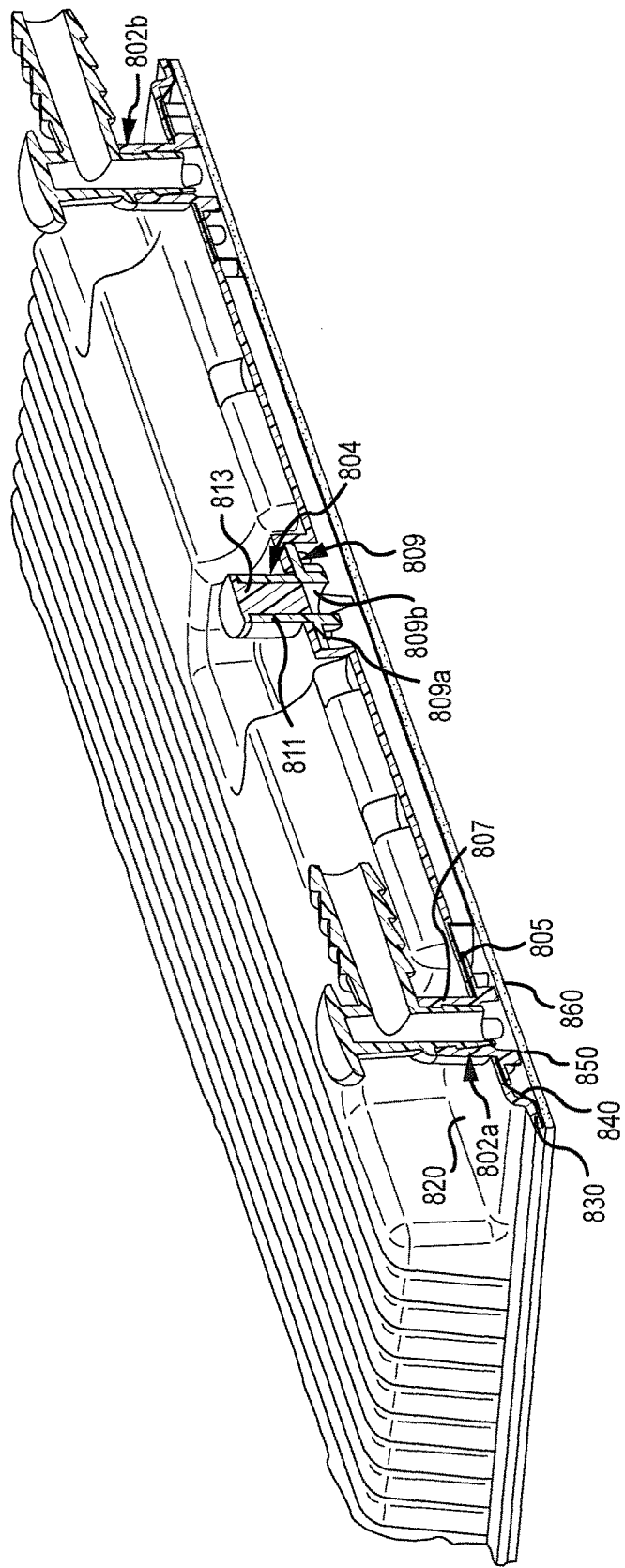
FIGS. 13A and 13B illustrate offset, widthwise, cross-sectional views of the medical pad embodiment shown in FIG. 8.
Figure 13B:
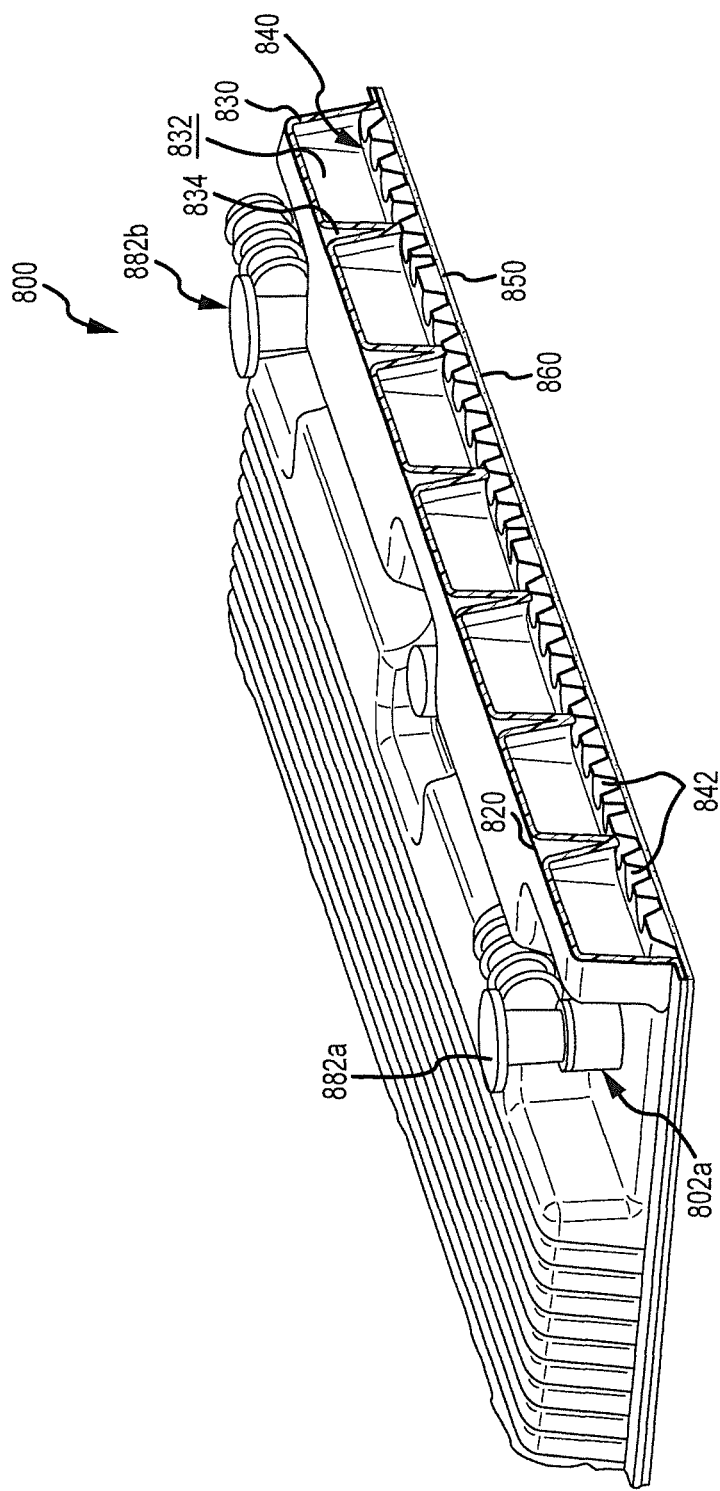

Reference is now made to FIGS. 13A and 13B which illustrate cross-sectional views of medical pad 800, with inlet port 802*a* and outlet port 802*b* thereof interconnected to connectors 882*a* and 882*b*, respectively. Fluid circulation lines 880*a* and 880*b* are not shown to facilitate discussion.

As shown in FIG. 13A, the enlarged ends 805 of inlet port 802*a* and outlet port 802*b* are positioned between fluid interface layer 850 and intermediate layer 840 to provide for a first thermal-exchange fluid flow in to and out of the circulation layer defined by interface layer 850 and intermediate layer 840. As noted, the stand-off members 805*b* maintain a minimum desired spacing to facilitate fluid flow in to and out of the fluid circulation layer. As further shown by FIG. 13A, fill port 804 may comprise and enlarged end 809 disposed between a bottom side of containment layer 830 and the top side of intermediate layer 840. The enlarged end 809 may include a disk portion 809*a*, an aperture 809*b* and stand-off members 809*c* projecting away from disk portion 809*a* about aperture 809*b*. The stand-off members 809*c* maintain a minimum desired spacing to facilitate fluid flow into the containment layer. The fill port 804 further includes tubular portion 811 for selective fluid interconnection to and disconnection from a source of the second thermal-exchange fluid during filling of the containment layer. A plug 813 may be provided to close-off tubular portion 811 after filling of the containment layer.

As may be appreciated, medical pad 800 may be readily assembled and readied for use. For example, interface layer 850 may be provided with a removable layer 860 removably attached to the bottom adhesive surface of the fluid interface layer. In turn, the top side of the fluid interface layer 850 may be interconnected to a bottom side of the intermediate layer 840 with enlarged ends 805 of ports 802*a* and 802*b* positioned therebetween, and tubular portions 807 located through openings 845, 835, and 825. Such interconnection may occur subsequent to or prior to interconnection of the top layer 820, containment layer 830, and intermediate layer 840 about the peripheries thereof. As may be appreciated, the enlarged end 809 of fill port 804 may be disposed between intermediate layer 840 and containment layer, with tubular portion positioned through openings 847, 837, and 827, prior to such interconnection.

Relatedly, prior to use, the second thermal-exchange fluid may be flowed through fill port 804 into the containment layer defined by containment layer 830 and intermediate layer 840. In this regard, the second thermal-exchange fluid may be introduced in a manner so that it flows through fill port 804, depressions 842 and in between the bottom side of containment layer 830 and top side of intermediate layer 840 to fill depressions 842 and at least a portion of the chambers 832 across the lateral entirety of the containment layer.

In one example, a vacuum may be initially established in the containment layer via use of fill port 804. In turn, fill port 804 may be interconnected to a source for the second thermal-exchange fluid. In one approach, a gel material (e.g., a cellulose gel comprising CMC, water and a cross-linking material such as aluminum acetate) may be employed. The gel may be flowed into the containment layer to fill depressions 842 and at least a portion of or substantially all of the volumes of chambers 832. Plug 813 may then be retainably inserted in fill port 804. In turn, the gel material may be allowed to cure, wherein cross-linking occurs so that gel material sets to maintain a shape defined by the volume of containment layer.

In contemplated arrangements, after filling the fluid containment layer with the second thermal-exchange fluid, the medical pad 800 may be cooled. By way of example, in some embodiments, medical pad may simply be disposed in a freezer, yielding the medical pad 800 ready for use.

At the time of use, bottom layer 860 may be removed from an adhesive surface on the bottom side of the fluid interface layer 850, and the adhesive surface of medical pad 800 may be contacted with a patient to initiate patient cooling. As may be appreciated, such patient cooling provides for thermal exchange between the second thermal-exchange fluid and the patient. Such thermal exchange may occur, for example, during transport of a patient.

Further, as and when patient cooling is desired via thermal exchange between a first thermal-exchange fluid circulated through medical pad 800 and a patient, connectors 882a, 882b of fluid circulation lines 880a, 880b may be interconnected to ports 802a, 802b, and connector 884 may be interconnected to a fluid circulation control system, wherein the first thermal-exchange fluid may be circulated through circulation layer of medical pad 800 to achieve patient cooling in tandem with or independent from patient cooling via the second thermal-exchange fluid (e.g., during and after the second thermal-exchange fluid warms).

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain known modes of practicing the invention and to enable others skilled in the art to utilize the invention in such or other embodiments and with various modifications required by the particular application(s) or use(s) of the present invention. It is intended that the appended claims be construed to include alternative embodiments to the extent permitted by the prior art.

Having described several embodiments, it will be recognized by those of skill in the art that various modifications, alternative constructions, and equivalents may be used without departing from the spirit of the invention. Accordingly, the above description should not be taken as limiting the scope of the invention, which is defined in the following claims.

What is claimed is:

1. A medical pad comprising:
   a first layer for containing a circulatable first thermal-exchange fluid for circulation therethrough, wherein the medical pad is operable for thermal exchange between said circulatable first thermal-exchange fluid and a patient through a first surface of the first layer on a first side of the first layer;
   a second layer disposed on a second side of the first layer and interconnected to the second side of the first layer, said second side of the first layer being opposite to the first side of the first layer, wherein the second layer encloses a non-cirulatable second thermal-exchange fluid therewithin, wherein the non-circulatable second thermal exchange fluid comprises a liquid, and wherein the second layer comprises:
      a plurality of portions, defined by a plurality of depressions, for containing at least a portion of said non-circulatable second thermal-exchange fluid therewithin, wherein the plurality of portions are located laterally adjacent to and side-by-side with corresponding portions of the first layer, and wherein the corresponding portions of the first layer comprise fluid flow channels extending between and around said plurality of depressions for circulation of the circulatable first thermal exchange fluid therethrough;
   wherein the medical pad is operable for thermal exchange between the second thermal-exchange fluid and a patient through said first surface of the first layer on said first side of the first layer.

2. The medical pad recited in claim 1, wherein said non-circulatable second thermal-exchange fluid has a freezing point of 0° C. or less.

3. The medical pad of claim 1, wherein bottom surfaces of the plurality of depressions are in contact with the first surface of the first layer.

4. The medical pad recited in claim 1, wherein greater than 30% of an area of the medical pad provided for contact with a patient is located adjacent to and thereby in thermal communication with the circulatable first thermal-exchange fluid.

5. The medical pad recited in claim 4, wherein approximately 50% of the area of the medical pad provided for contact with a patient is located adjacent to and thereby in thermal communication with the circulatable first thermal-exchange fluid.

6. The medical pad recited in claim 4, wherein greater than 30% of the area of the medical pad provided for contact with a patient is located adjacent to and thereby in thermal communication with the non-circulatable second thermal-exchange fluid.

7. The medical pad recited in claim 4, wherein approximately 50% of the area of the medical pad provided for contact with a the patient is located adjacent to and thereby in thermal communication with the non-circulatable second thermal-exchange fluid.

8. The medical pad recited in claim 1, wherein approximately 50% of an area of the medical pad provided for contact with a patient is located adjacent to and thereby in thermal communication with the circulatable first thermal-exchange fluid and approximately 50% of the area of the medical pad provided for contact with a patient is located adjacent to and thereby in thermal communication with the non-circulatable second thermal-exchange fluid.

9. The medical pad recited in claim 1, wherein the second layer extends across at least a majority of a lateral extent of the first layer.

10. The medical pad recited in claim 1, wherein the second layer comprises a plurality of chambers for containing at least a portion of said non-circulatable second thermal-exchange fluid therewithin.

11. The medical pad recited in claim 10, wherein the plurality of chambers comprise a plurality of enclosed chambers each enclosing a corresponding different portion of the second thermal-exchange fluid therewithin.

12. The medical pad recited in claim 11, wherein at least a portion of each of the plurality of enclosed chambers is defined by a corresponding different portion of a pliable member.

13. The medical pad recited in claim 10, wherein each of the plurality of chambers projects away from the second side of the first layer with indentations formed between adjacent ones of the plurality of chambers.

14. The medical pad recited in claim 10, wherein the plurality of chambers define a waffle-shaped configuration.

15. The medical pad recited in claim 10, wherein the second layer extends across at least a majority of a lateral extent of the first layer.

16. The medical pad recited in claim 10, further comprising:
an insulative layer extending over said plurality of chambers to insulate said second layer.

17. The medical pad recited in claim 16, wherein the first surface of the first layer is an adhesive surface adapted for releasable adhesive contact with skin of a patient.

18. The medical pad recited in claim 1, wherein the first surface of the first layer is an adhesive surface adapted for releasable adhesive contact with skin of a patient.

19. The medical pad recited in claim 18, wherein the first and second layers are adapted to allow for conformal contact between the adhesive surface and the skin of the patient.

20. The medical pad recited in claim 1, further comprising:
a first port fluidly interconnected to the first layer for circulating the first thermal-exchange fluid into the first layer; and
a second port fluidly interconnected to the first layer for circulating the first thermal-exchange fluid out of the first layer.

21. The medical pad recited in claim 20, wherein said first port and said second port each extend away from the second side of the first layer, through openings formed through the second layer.

22. The medical pad recited in claim 1, wherein said second thermal-exchange fluid comprises the liquid in a gel form.

23. The medical pad recited in claim 22, wherein said liquid in the gel form is shape-holding.

24. The medical pad recited in claim 1, wherein at least one of the circulatable first thermal-exchange fluid or the non-circulatable second thermal-exchange fluid has a thermal conductivity that exceeds 5.0 W/mK.

25. The medical pad recited in claim 24, wherein the at least one of the circulatable first thermal-exchange fluid or the non-circulatable second thermal-exchange fluid comprises a liquid containing a material having a thermal conductivity that exceeds a thermal conductivity of the liquid by at least a factor of 100.

26. The medical pad recited in claim 1, wherein the second layer further comprises:
a fill port for use in filling the second layer with said non-circulatable second thermal-exchange fluid; and,
a plug to close the fill port after said filling.

27. The medical pad recited in claim 1, wherein the second layer further comprises a plurality of chambers for containing at least a portion of said non-circulatable second thermal-exchange fluid therewithin, and wherein the plurality of depressions and plurality of chambers are disposed in opposed, face-to-face relation for fluid communication therebetween.

28. The medical pad as recited in claim 1, wherein said plurality of depressions and said fluid flow channels are defined by a structure having a dimple matrix.

29. A medical pad comprising:
a first layer for containing a circulatable first thermal-exchange fluid for circulation therethrough, wherein the medical pad is operable for thermal exchange between said circulatable first thermal-exchange fluid and a patient on a first side of the first layer;
a second layer disposed on a second side of the first layer, said second side of the first layer being opposite to the first side of the first layer, wherein the second layer encloses a non-circulatable second thermal-exchange fluid therewithin, wherein the non-circulatable second thermal exchange fluid comprises a liquid, and wherein the second layer comprises:
a plurality of portions, defined by a plurality of depressions, for containing at least a portion of said non-circulatable second thermal-exchange fluid, wherein the plurality of portions are located laterally adjacent to and side-by-side with corresponding portions of the first layer, and wherein the corresponding portions of the first layer comprise fluid flow channels extending between said plurality of depressions for circulation of the circulatable first thermal exchange fluid therethrough;
wherein the medical pad is operable for thermal exchange between the non-circulatable second thermal-exchange fluid and a patient on said first side of the first layer;
a first port fluidly interconnected to the first layer for circulating the circulatable first thermal-exchange fluid into the first layer; and,
a second port fluidly interconnected to the first layer for circulating the circulatable first thermal-exchange fluid out of the first layer, wherein said first port and said second port each extend away from the second side of the first layer through openings formed through the second layer.

* * * * *

UNITED STATES PATENT AND TRADEMARK OFFICE
CERTIFICATE OF CORRECTION

PATENT NO.       : 9,687,386 B2
APPLICATION NO.  : 13/230663
DATED            : June 27, 2017
INVENTOR(S)      : Gary A. Carson It is certified that error appears in the above-identified patent and that said Letters Patent is hereby corrected as shown below:

In the Specification

Column 9, Line 26, delete "they mal-" and insert --thermal--

In the Claims

Claim 1, Column 18, Line 20, delete "cirulatable" and insert --circulatable--
Claim 7, Column 18, Line 62, after "contact with a" delete "the"

Signed and Sealed this
Twenty-second Day of August, 2017

Joseph Matal
*Performing the Functions and Duties of the*
*Under Secretary of Commerce for Intellectual Property and*
*Director of the United States Patent and Trademark Office*